US009124896B2

(12) United States Patent
Kondo et al.

(10) Patent No.: US 9,124,896 B2
(45) Date of Patent: *Sep. 1, 2015

(54) MOTION VECTOR CODING METHOD AND MOTION VECTOR DECODING METHOD

(71) Applicant: Panasonic Intellectual Property Corporation of America, Torrance, CA (US)

(72) Inventors: Satoshi Kondo, Kyoto (JP); Shinya Kadono, Fukuoka (JP); Makoto Hagai, Osaka (JP); Kiyofumi Abe, Osaka (JP)

(73) Assignee: PANASONIC INTELLECTUAL PROPERTY CORPORATION OF AMERICA, Torrance, CA (US)

( * ) Notice: Subject to any disclaimer, the term of this patent is extended or adjusted under 35 U.S.C. 154(b) by 0 days.
This patent is subject to a terminal disclaimer.

(21) Appl. No.: 14/533,318

(22) Filed: Nov. 5, 2014

(65) Prior Publication Data

US 2015/0055714 A1  Feb. 26, 2015

Related U.S. Application Data

(60) Division of application No. 13/966,484, filed on Aug. 14, 2013, now Pat. No. 8,908,769, which is a division of application No. 11/979,013, filed on Oct. 30, 2007, now abandoned, which is a continuation of application No. 10/468,203, filed as application No. PCT/JP03/00055 on Jan. 8, 2003, now Pat. No. 7,362,807.

(30) Foreign Application Priority Data

Jan. 9, 2002   (JP) .................. 2002-001983
Jul. 12, 2002  (JP) .................. 2002-204714
Nov. 28, 2002  (JP) .................. 2002-346062

(51) Int. Cl.
*H04N 19/176* (2014.01)
*H04N 19/52* (2014.01)
(Continued)

(52) U.S. Cl.
CPC ............. *H04N 19/52* (2014.11); *H04N 19/137* (2014.11); *H04N 19/139* (2014.11);
(Continued)

(58) Field of Classification Search
CPC . H04N 19/176; H04N 19/513; H04N 19/137; H04N 19/139; H04N 19/50; H04N 19/51; H04N 19/517; H04N 19/52; H04N 19/521; H04N 19/533; H04N 19/537; H04N 19/56; H04N 19/577; H04N 19/593; H04N 19/61
USPC ...................................................... 375/240.16
See application file for complete search history.

(56) References Cited

U.S. PATENT DOCUMENTS 5,428,403 A     6/1995  Andrew et al.
5,905,535 A *   5/1999  Kerdranvat ................ 348/416.1
(Continued)

FOREIGN PATENT DOCUMENTS

CN     1132983    10/1996
EP    0 651 574    5/1995
(Continued)

OTHER PUBLICATIONS

"Joint Video Team (JVT) of ISO/IEC MPEG and ITU-T-VCEG", pp. 1-78, Pattaya, Thailand, Dec. 3-7, 2001.
(Continued)

*Primary Examiner* — Mohammed Rahaman
(74) *Attorney, Agent, or Firm* — Wenderoth, Lind & Ponack, L.L.P.

(57) ABSTRACT

A motion vector coding unit executes processing including a neighboring block specification step of specifying a neighboring block which is located in the neighborhood of a current block; a judgment step of judging whether or not the neighboring block has been coded using a motion vector of another block; a prediction step of deriving a predictive motion vector of the current block using a motion vector calculated from the motion vector of the other block as a motion vector of the neighboring block; and a coding step of coding the motion vector of the current block using the predictive motion vector.

2 Claims, 22 Drawing Sheets

(51) Int. Cl.

| | |
|---|---|
| H04N 19/56 | (2014.01) |
| H04N 19/50 | (2014.01) |
| H04N 19/51 | (2014.01) |
| H04N 19/513 | (2014.01) |
| H04N 19/61 | (2014.01) |
| H04N 19/593 | (2014.01) |
| H04N 19/517 | (2014.01) |
| H04N 19/577 | (2014.01) |
| H04N 19/137 | (2014.01) |
| H04N 19/139 | (2014.01) |
| H04N 19/537 | (2014.01) |
| H04N 19/533 | (2014.01) |

(52) U.S. Cl.
CPC ............ *H04N 19/176* (2014.11); *H04N 19/50* (2014.11); *H04N 19/51* (2014.11); *H04N 19/513* (2014.11); *H04N 19/517* (2014.11); *H04N 19/521* (2014.11); *H04N 19/533* (2014.11); *H04N 19/537* (2014.11); *H04N 19/56* (2014.11); *H04N 19/577* (2014.11); *H04N 19/593* (2014.11); *H04N 19/61* (2014.11)

(56) References Cited

U.S. PATENT DOCUMENTS

| | | | |
|---|---|---|---|
| 5,991,447 | A | 11/1999 | Eifrig et al. |
| 6,005,980 | A * | 12/1999 | Eifrig et al. ............... 382/236 |
| 6,097,842 | A | 8/2000 | Suzuki et al. |
| 6,272,179 | B1 | 8/2001 | Kadono |
| 6,654,420 | B1 | 11/2003 | Snook |
| 6,671,319 | B1 * | 12/2003 | Chang et al. ............. 375/240.16 |
| 6,842,483 | B1 | 1/2005 | Au et al. |
| 6,983,018 | B1 | 1/2006 | Lin et al. |
| 7,020,200 | B2 | 3/2006 | Winger |
| 8,111,754 | B1 | 2/2012 | Demos |
| 2002/0176505 | A1 | 11/2002 | Kim et al. |
| 2003/0206589 | A1 | 11/2003 | Jeon |

FOREIGN PATENT DOCUMENTS

| | | |
|---|---|---|
| EP | 0 765 087 | 3/1997 |
| EP | 1 335 609 | 8/2003 |
| JP | 11-317961 | 11/1999 |
| JP | 2000-099864 | 4/2000 |
| JP | 2000-299864 | 10/2000 |
| JP | 2001-45498 | 2/2001 |
| JP | 2001-224036 | 8/2001 |
| KR | 1020020077630 | 10/2002 |
| WO | 94/22269 | 9/1994 |
| WO | 00/33581 | 6/2000 |
| WO | 01/33864 | 5/2001 |
| WO | 01/50770 | 7/2001 |

OTHER PUBLICATIONS

Notice of Allowance dated Jun. 5, 2012 in U.S. Appl. No. 12/691,195, filed Jan. 21, 2010.

Canadian Office Action dated Dec. 13, 2013 in Canadian Application No. 2,762,023.

H.26L Test Model Long Term No. 6 (TML-6) Draft "0", ITU-T Telecommunication Standardization Sector of ITU, Geneva, CH, Jan. 9, 2001, pp. 1-35, XP001089815.

Information Technology—Coding of Audio-Visual Objects—Part 2: Visual, (ISO/IEC 14496.2), pp. 146-148, Dec. 1, 1999.

European Search Report filed in European Application No. 03 70 0472 dated Feb. 28, 2006.

International Search Report issued in PCT/JP03/00055.

Japanese Office Action issued on Jul. 24, 2007 in corresponding Japanese Patent Application No. 2002-346062.

European Office Action issued Apr. 20, 2009 in the corresponding European Patent Application No. 03 700 472.8.

Alexis Michael Tourapis, Jizheng Xu, Feng Wu, and Shipeng Li, "Motion Vector Prediction in Bidirentionally Predictive (B) frames with regards to Direct Mode", Joint Video Team (JVT) of ISO/IEC MPEG & ITU-T VCEG (ISO/IEC JTC1/SC29/WG11 and ITU-T SG16 Q.6), May 2002, pp. 1-7.

Office Action dated Dec. 23, 2011 in U.S. Appl. No. 11/979,012.

Office Action dated Dec. 29, 2011 in U.S. Appl. No. 11/979,010.

European Office Action issued Apr. 3, 2012 in European Application No. 10 187 172.1 which is a foreign counterpart of the present application.

"Text of ISO/IEC 14496-10 CD Advanced Video Coding", 60. MPEG Meeting; Jun. 5, 2002-Oct. 5, 2002; Fairfax, (Motion Picture Expert Group or ISO/IEC JTC1/SC29/WG11), No. N4810, May 14, 2002, XP30012280, ISSN: 0000-0366, pp. BSN1-BSN142.

European Result of Consultation issued Sep. 21, 2012 in European Application No. 10 169 925.4.

European Office Action issued Sep. 26, 2012 in European Application No. 10 169 923.9.

European Office Action issued Sep. 26, 2012 in European Application No. 10 169 924.7.

European Office Action issued Sep. 26, 2012 in European Application No. 10 187 151.5.

European Office Action issued Sep. 26, 2012 in European Application No. 10 187 172.1.

Kadono et al., "Memory Reduction for Temporal Technique of Direct Mode", 5. JVT Meeting; Oct. 14, 2002-Oct. 18, 2002; Geneva, CH; (Joint Video Team of ISO/IEC JTC1/SC29/WG11 and ITU-T SG. 16), No. JVT-E076, Oct. 18, 2002, XP030005493; ISSN: 0000-0432.

Weigand, "Editor's Proposed Text Modifications"; 4. JVT Meeting; 61. MPEG Meeting; Jul. 22, 2002-Jul. 26, 2002; Klagenfurt, AT; (Joint Video Team of ISO/IEC JTC1/SC29/WG11 and ITU-T SG. 16), No. JVT-D015d5, Jul. 26, 2002, XP030005290, ISSN: 0000-0441.

Tourapis et al., "MV Pred.: Time-Indep., Divide-Free, Perf. Impr. & Bug Fix", 4. JVT Meeting; 61. MPEG Meeting; Jul. 22, 2002-Jul. 26, 2002; Klagenfurt, AT; (Joint Video Team of ISO/IEC JTC1/SC29/WG11 and ITU-T SG. 16), No. JVT-D040, Jul. 26, 2002, EXP030005314, ISSN: 0000-0441.

Office Action dated Aug. 30, 2013 in U.S. Appl. No. 11/979,013, filed Oct. 30, 2007.

\* cited by examiner

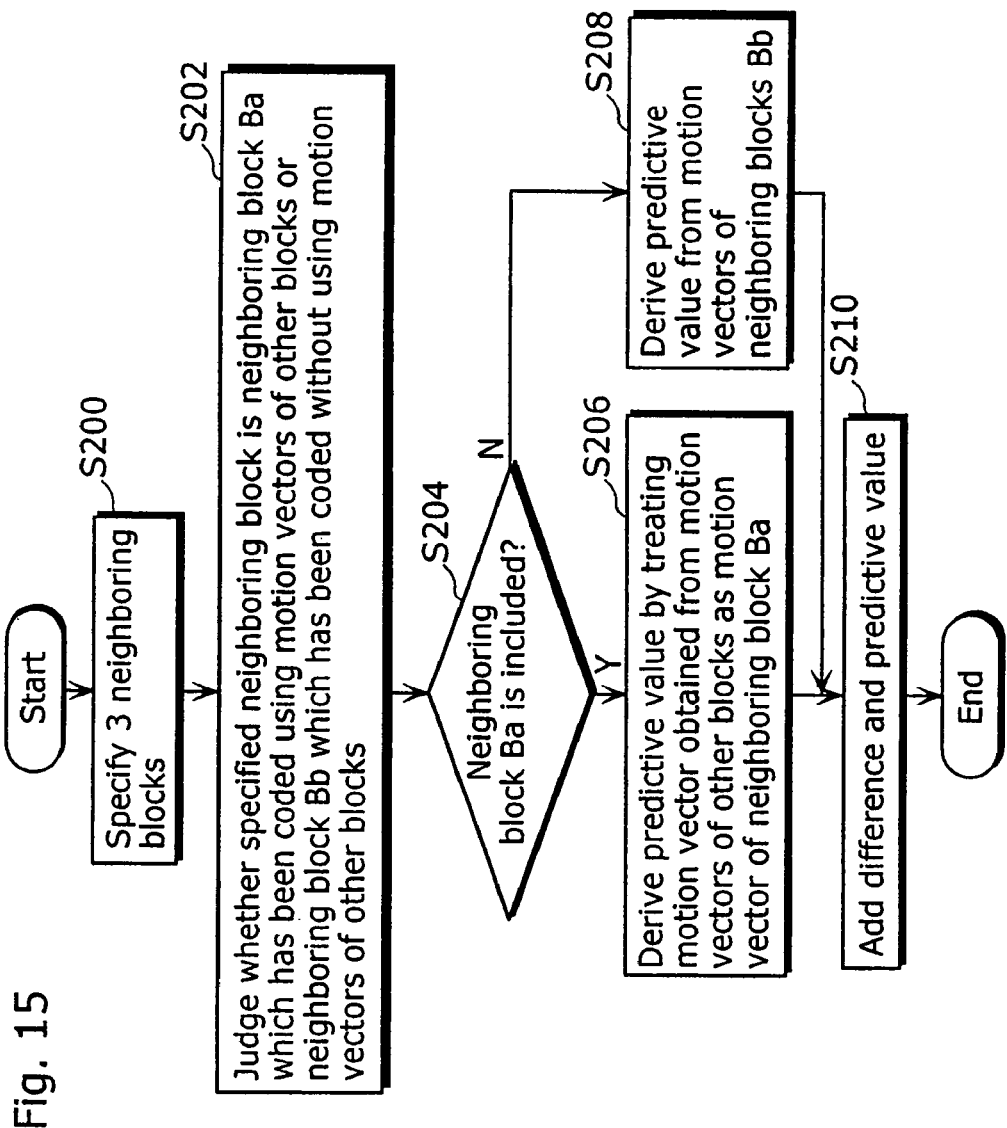

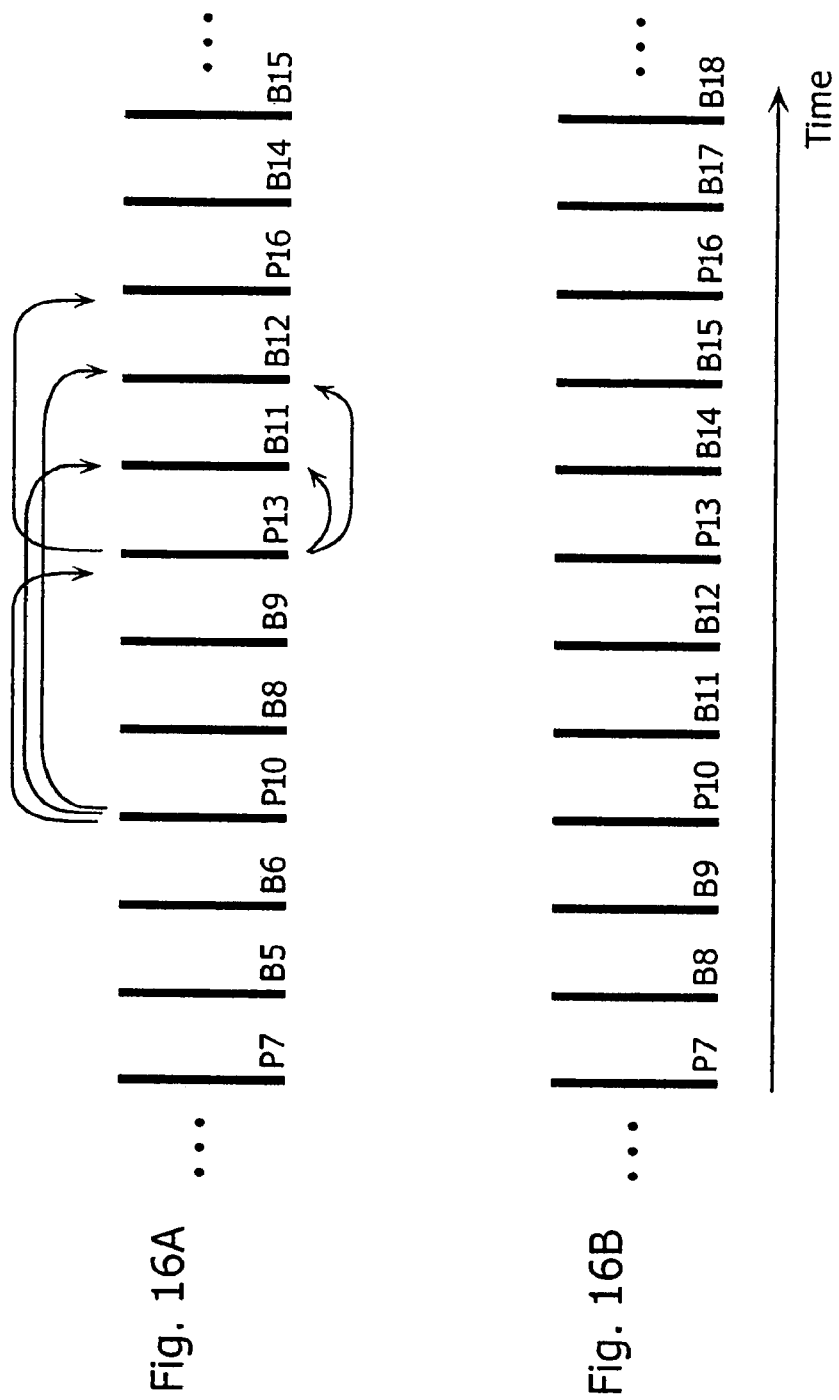

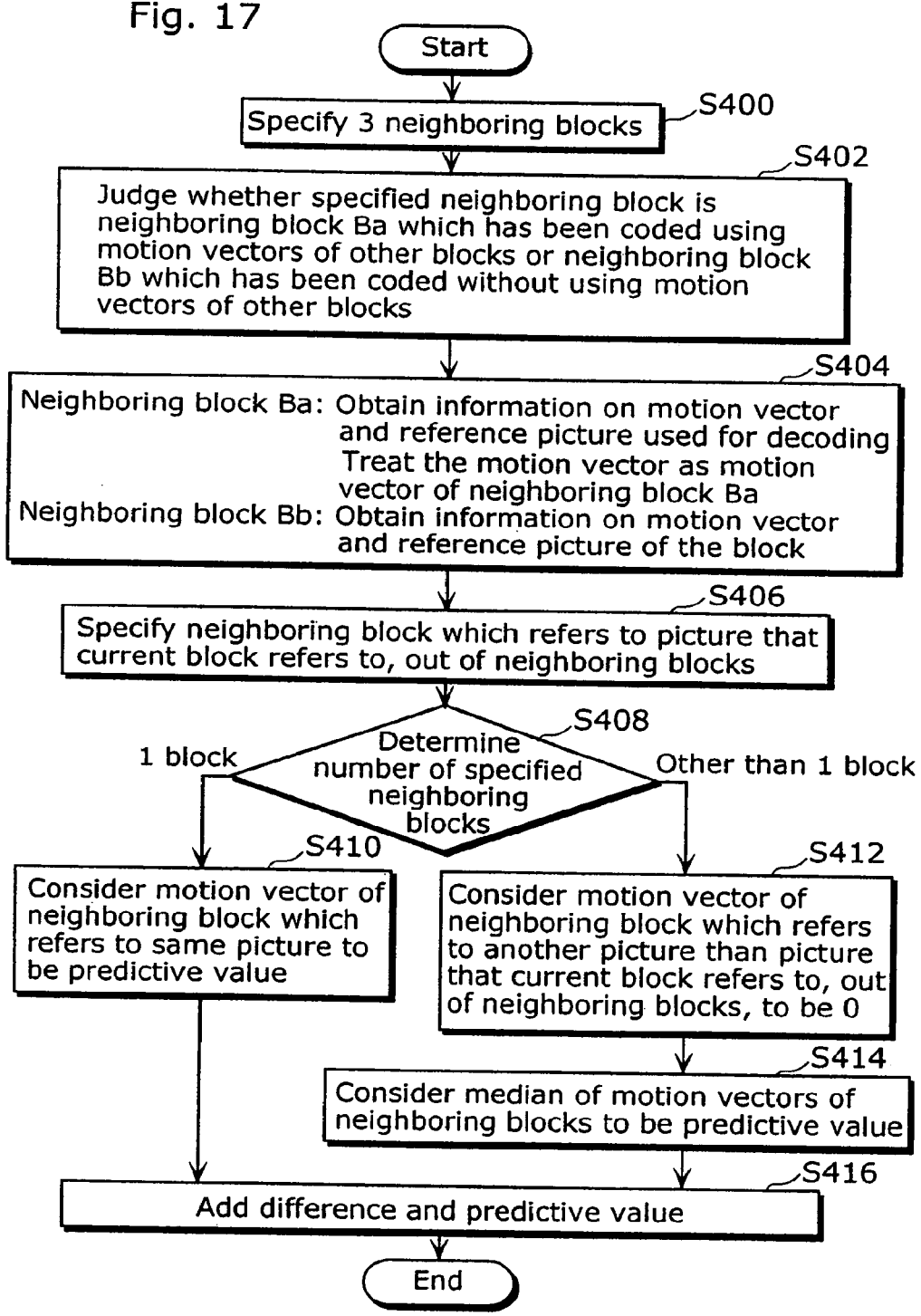

MOTION VECTOR CODING METHOD AND MOTION VECTOR DECODING METHOD

BACKGROUND OF THE INVENTION

1. Technical Field

The present invention relates to a motion vector coding method and a motion vector decoding method using inter picture prediction coding.

2. Background Art

In the age of multimedia which integrally handles audio, video and other information, existing information media, i.e., newspapers, magazines, televisions, radios, telephones and other means through which information is conveyed to people, have recently come to be included in the scope of multimedia. Generally, multimedia refers to something that is represented by associating not only characters, but also graphics, voices, and especially pictures and the like together, but in order to include the aforementioned existing information media in the scope of multimedia, it appears as a prerequisite to represent such information in digital form.

However, when calculating the amount of information contained in each of the aforementioned information media as the amount of digital information, while the amount of information per character is 1~2 bytes, the amount of information to be required for voice is 64 Kbits or over per second (telephone quality), and 100 Mbits or over per second for moving pictures (current television reception quality), and it is not realistic for the aforementioned information media to handle such an enormous amount of information as it is in digital form. For example, although video phones are already in actual use via Integrated Services Digital Network (ISDN) which offers a transmission speed of 64 Kbps/s~1.5 Mbps/s, it is not practical to transmit video shot by television cameras directly through ISDN.

Against this backdrop, information compression techniques have become required, and moving picture compression techniques compliant with H.261 and H.263 standards internationally standardized by ITU-T (International Telecommunication Union—Telecommunication Standardization Sector) are employed for video phones, for example (See, for example, Information technology—Coding of audio-visual objects—Part 2: video (ISO/IEC 14496-2), pp. 146-148, 1999. 12. 1). Moreover, according to information compression techniques compliant with the MPEG-1 standard, it is possible to store picture information in an ordinary music CD (compact disc) together with sound information.

Here, MPEG (Moving Picture Experts Group) is an international standard on compression of moving picture signals, and MPEG-1 is a standard for compressing television signal information approximately into one hundredth so that moving picture signals can be transmitted at a rate of 1.5 Mbps. Furthermore, since transmission speed within the scope of the MPEG-1 standard is limited primarily to about 1.5 Mbps, MPEG-2, which was standardized with a view to satisfy requirements for further improved picture quality, allows data transmission of moving picture signals at a rate of 2~15 Mbps. Furthermore, MPEG-4 which achieves a higher compression ratio than that of MPEG-1 and MPEG-2, allows coding, decoding and operation in an object unit, and realizes a new function required for the multimedia age, has been standardized by the working group (ISO/IEC JTC1/SC29/WG11) which has been engaged in the standardization of MPEG-1 and MPEG-2. MPEG-4 was initially aimed at standardization of a coding method for a low bit rate, but now it is extended to standardization of a more versatile coding method for moving pictures further including interlace images and higher bit rates.

In the above-mentioned moving picture coding, the amount of information is compressed by exploiting redundancies in the spatial and temporal directions. Here, inter picture prediction coding is used as a method of using the temporal redundancies. In the inter picture prediction coding, a picture is coded using a temporarily forward or backward picture as a reference picture. The motion (a motion vector) of the current picture to be coded from the reference picture is estimated, and the difference between the picture obtained by the motion compensation and the current picture is calculated. Then, the spatial redundancies are eliminated from this difference, so as to compress the information amount of the moving picture.

In a moving picture coding method in compliance with MPEG-1, MPEG-2, MPEG-4, H.263, H.26L or the like, a picture which is not inter picture prediction coded, namely, which is intra picture coded, is called an I-picture. Here, a picture means a single coding unit including both a frame and a field. Also, a picture which is inter picture prediction coded with reference to one picture is called a P-picture, and a picture which is inter picture prediction coded with reference to two previously processed pictures is called a B-picture.

FIG. 1 is a diagram showing a predictive relation between pictures in the above-mentioned moving picture coding method.

In FIG. 1, a vertical line indicates one picture, with a picture type (I, P or B) indicated at the lower right thereof. Also, FIG. 1 indicates that a picture pointed by an arrow is inter picture prediction coded using a picture located at the other end of the arrowhead as a reference picture. For example, a B-picture which is the second from the left is coded using the first I-picture and the fourth P-picture as reference pictures.

In the moving picture coding method in compliance with MPEG-4, H.26L or the like, a coding mode called direct mode can be selected for coding a B-picture.

An inter picture prediction coding method in direct mode will be explained with reference to FIG. 2.

FIG. 2 is an illustration for explaining the inter picture prediction coding method in direct mode.

It is now assumed that a block C in a picture B3 is coded in direct mode. In this case, a motion vector MVp of a block X in a reference picture (a picture P4 that is a backward reference picture, in this case) which has been coded immediately before the picture B3 is exploited, where the block X is co-located with the block C. The motion vector MVp is a motion vector which was used when the block X was coded, and refers to a picture P1. The block C is bi-directionally predicted from the reference pictures, namely, the picture P1 and the picture P4, using motion vectors parallel to the motion vector MVp. The motion vectors used for coding the block C are, in this case, a motion vector MVFc for the picture P1 and a motion vector MVBc for the picture P4.

In the moving picture coding method in compliance with MPEG-4, H.26L or the like, a difference between a predictive value obtained from motion vectors of neighboring blocks and a motion vector of a current block to be coded is coded for coding the motion vector. In the following description, a "predictive value" indicates a predictive value of a motion vector. Since motion vectors of neighboring blocks have similar direction and motion in many cases, the amount of coding the motion vector can be reduced by coding the difference from the predictive value obtained from the motion vectors of the neighboring blocks.

Here, a motion vector coding method in MPEG-4 will be explained with reference to FIGS. 3A-3D.

FIGS. 3A-D are illustrations for explaining a method for coding a motion vector MV of a current block A to be coded in MPEG-4.

In FIGS. 3A~3D, blocks indicated by a thick line are macroblocks of 16×16 pixels, and there exist 4 blocks of 8×8 pixels in each macroblock. Here, it is assumed that a motion vector is obtained at a level of a block of 8×8 pixels.

As shown in FIG. 3A, as for a current block A located at the upper left in a macroblock, a difference between a predictive value and a motion vector MV of the current block A is coded, where the predictive value is calculated from a motion vector MVb of a neighboring block B to the left of the current block A, a motion vector MVc of a neighboring block C just above the current block A and a motion vector MVd of a neighboring block D above and to the right of the current block A.

Similarly, as shown in FIG. 3B, as for a current block A located at the upper right in a macroblock, a difference between a predictive value and a motion vector MV of the current block A is coded, where the predictive value is calculated from a motion vector MVb of a neighboring block B to the left of the current block A, a motion vector MVc of a neighboring block C just above the current block A and a motion vector MVd of a neighboring block D above and to the right of the current block A.

As shown in FIG. 3C, as for a current block A located at the lower left in a macroblock, a difference between a predictive value and a motion vector MV of the current block A is coded, where the predictive value is calculated from a motion vector MVb of a neighboring block B to the left of the current block A, a motion vector MVc of a neighboring block C just above the current block A and a motion vector MVd of a neighboring block D above and to the right of the current block A.

As shown in FIG. 3D, as for a current block A located at the lower right in a macroblock, a difference between a predictive value and a motion vector MV of the current block A is coded, where the predictive value is calculated from a motion vector MVb of a neighboring block B to the left of the current block A, a motion vector MVc of a neighboring block C above and to the left of the current block A and a motion vector MVd of a neighboring block D just above the current block A. Here, the predictive value is calculated using the medians obtained from the horizontal and vertical components of these three motion vectors MVb, MVc and MVd respectively.

Next, a motion vector coding method in H.26L which has been developed for standardization will be explained with reference to FIG. 4.

FIG. 4 is an illustration for explaining a method for coding a motion vector MV of a current block A in H.26L.

A current block A is a block of 4×4 pixels, 8×8 pixels or 16×16 pixels, and a motion vector of this current block A is coded using a motion vector of a neighboring block B including a pixel b located to the left of the current block A, a motion vector of a neighboring block C including a pixel c located just above the current block A and a motion vector of a neighboring block D including a pixel d located above and to the right of the current block A. Note that the sizes of the neighboring blocks B, C and D are not limited to those as shown in FIG. 4 by dotted lines.

FIG. 5 is a flowchart showing the procedure of coding the motion vector MV of the current block A using the motion vectors of the neighboring blocks as mentioned above.

First, the neighboring block which refers to the picture that the current block A refers to is specified out of the neighboring blocks B, C and D (Step S502), and the number of specified neighboring blocks is determined (Step S504).

When the number of the neighboring blocks determined in Step S504 is 1, the motion vector of that neighboring block which refers to the same picture is considered to be a predictive value of the motion vector MV of the current block A (Step S506).

When the number of the neighboring blocks determined in Step S505 is another value other than 1, the motion vector of the neighboring block which refers to another picture other than the picture that the current block A refers to, out of the neighboring blocks B, C and D, is considered to be 0 (Step S507). And the median of the motion vectors of the neighboring blocks B, C and D is considered to be a predictive value of the motion vector of the current block A (Step S508).

Using the predictive value derived in Step S506 or Step S508 in this manner, the difference between the predictive value and the motion vector MV of the current block A is calculated and the difference is coded (Step S510).

As described above, in the motion vector coding methods in compliance with MPEG-4 and H.26L, motion vectors of neighboring blocks are exploited when coding a motion vector of a current block to be coded.

However, there are cases where motion vectors of neighboring blocks are not coded. For example, they are cases where a neighboring block is intra picture coded, a B-picture is coded in direct mode, and a P-picture is coded in skip mode. In these cases, the neighboring blocks are coded using the motion vectors of other blocks except when they are intra picture coded, namely, the neighboring blocks are coded using their own motion vectors based on the result of motion estimation.

So, according to the above-mentioned traditional motion vector coding method, a motion vector of a current block is coded as follows: When there exists one neighboring block, out of three neighboring blocks, which has no motion vector based on the above result of motion estimation and has been coded using motion vectors of other blocks, the motion vector of that neighboring block is considered to be 0. When there exist two such neighboring blocks, the motion vector of the remaining one neighboring block is used as a predictive value. And when there exist three neighboring blocks, the motion vector is coded considering a predictive value to be 0.

However, in direct mode or skip mode, motion compensation is actually performed as is the case where a motion vector of a neighboring block itself is used based on the estimation result, although the motion vector information is not coded. As a result, in the above traditional method, if a neighboring block is coded in direct mode or skip mode, the motion vector of the neighboring block is not used as a candidate for a predictive value. So, there is a problem of causing an inaccurate predictive value of a motion vector when coding the motion vector, and thus causing lower coding efficiency.

The present invention is conceived to solve this problem, and the object thereof is to provide a motion vector coding method and a motion vector decoding method for obtaining a more accurate predictive value for higher coding efficiency.

SUMMARY OF INVENTION

In order to achieve the above object, the motion vector coding method according to the present invention is a motion vector coding method for coding a motion vector of a current block in a moving picture, comprising: a neighboring block specification step of specifying a neighboring block which is located in the neighborhood of the current block and has already been coded; a judgment step of judging whether or not the neighboring block has been coded using a motion vector of another block; a prediction step of deriving a predictive motion vector of the current block using a motion vector calculated from the motion vector of said another block as a motion vector of the neighboring block, when it is judged in the judgment step that the neighboring block has been coded using the motion vector of said another block; and a coding step of coding the motion vector of the current block using the predictive motion vector.

As a result, when a motion vector of a current block is coded using a predictive motion vector derived from motion vectors of neighboring blocks, if any of the neighboring blocks has been coded using motion vectors of other blocks, the motion vector of the neighboring block is not considered to be 0 but to be the motion vector calculated from the motion vectors of the other blocks. Therefore, a more accurate predictive motion vector can be obtained, and thus efficiency of coding the motion vector can be improved.

Also, the motion vector decoding method according to the present invention is a motion vector decoding method for decoding a coded motion vector of a current block in a moving picture, comprising: a neighboring block specification step of specifying a neighboring block which is located in the neighborhood of the current block and has already been decoded, a judgment step of judging whether or not the neighboring block has been coded using a motion vector of another block; a prediction step of deriving a predictive motion vector of the current block using a motion vector calculated from the motion vector of said another block as a motion vector of the neighboring block, when it is judged in the judgment step that the neighboring block has been coded using the motion vector of said another block; and a decoding step of decoding the coded motion vector of the current block using the predictive motion vector.

As a result, the motion vector which has been coded according to the motion vector coding method of the present invention can be properly decoded, and thus the practical value thereof is high.

Note that the present invention can also be realized as a moving picture coding apparatus and a program using the above-mentioned motion vector coding method, and a storage medium storing the program, and a motion picture decoding apparatus and a program using the above-mentioned motion vector decoding method, and a storage medium storing the program.

BRIEF DESCRIPTION OF DRAWINGS

FIG. 15 is a flowchart showing an operation of a motion vector decoding unit in the second embodiment.

FIGS. 16A and 16B are illustrations for explaining how the pictures are inputted to and outputted from the moving picture decoding apparatus in the second embodiment.

FIG. 17 is a flowchart showing another operation of the motion vector decoding unit in the second embodiment.

DETAILED DESCRIPTION OF THE INVENTION

First Embodiment

A moving picture coding apparatus in a first embodiment of the present invention will be explained with reference to the figures.

Figure 6:
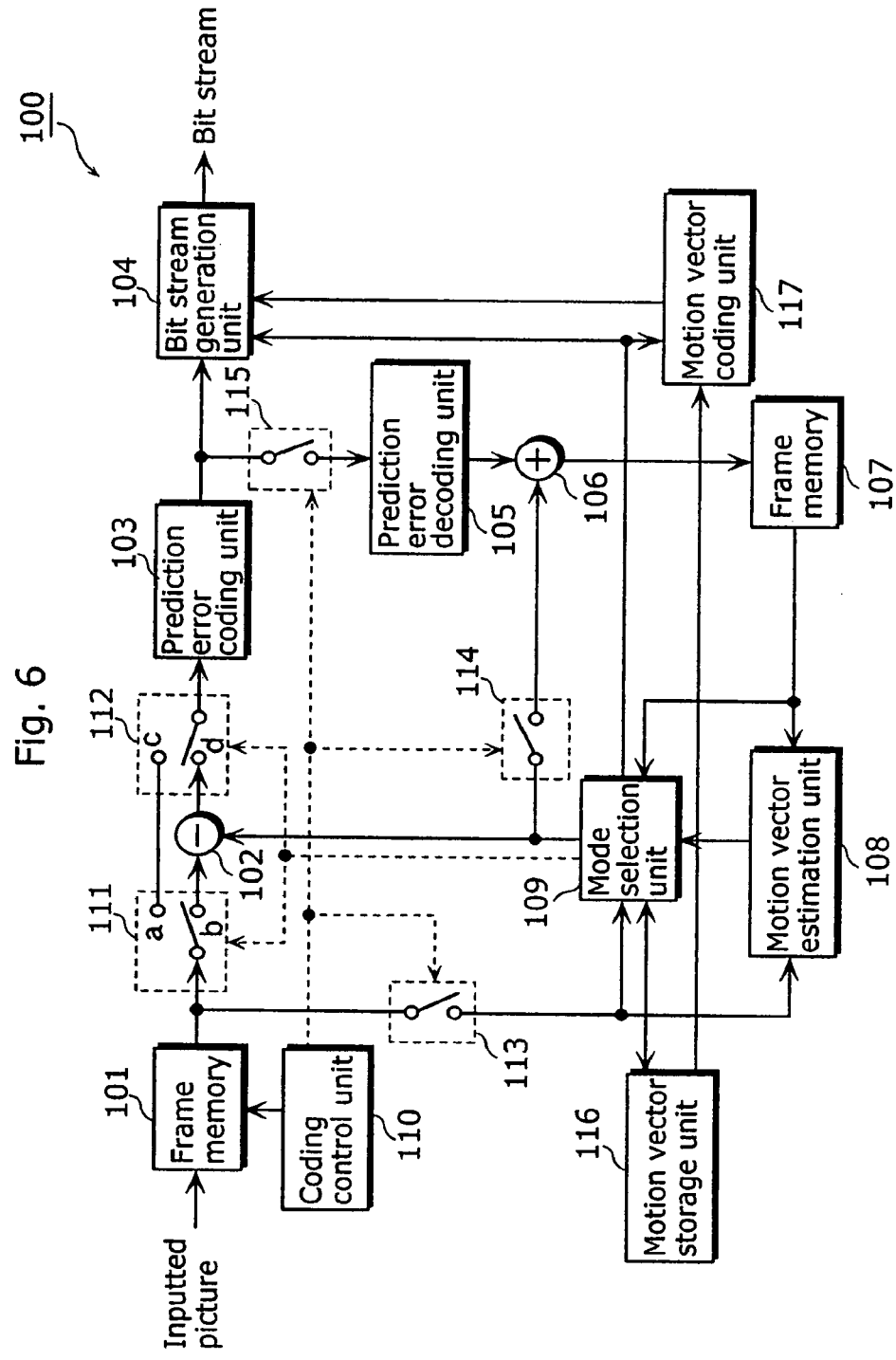
FIG. 6 is a block diagram showing a structure of a moving picture coding apparatus in a first embodiment of the present invention.

FIG. 6 is a block diagram of the moving picture coding apparatus in the first embodiment of the present invention.

This moving picture coding apparatus 100 aims at improving coding efficiency by improving accuracy of a predictive value of a motion vector, and includes a frame memory 101, a difference calculation unit 102, a prediction error coding unit 103, a bit stream generation unit 104, a prediction error decoding unit 105, an addition unit 106, a frame memory 107, a motion vector estimation unit 108, a mode selection unit 109, a coding control unit 110, switches 111~115, a motion vector storage unit 116 and a motion vector coding unit 117.

The frame memory 101 is a picture memory for holding inputted pictures on a picture-by-picture basis, and reorders the pictures inputted and obtained in order of time into coding order for output. The pictures are reordered under the control of the coding control unit 110.

Figure 7:
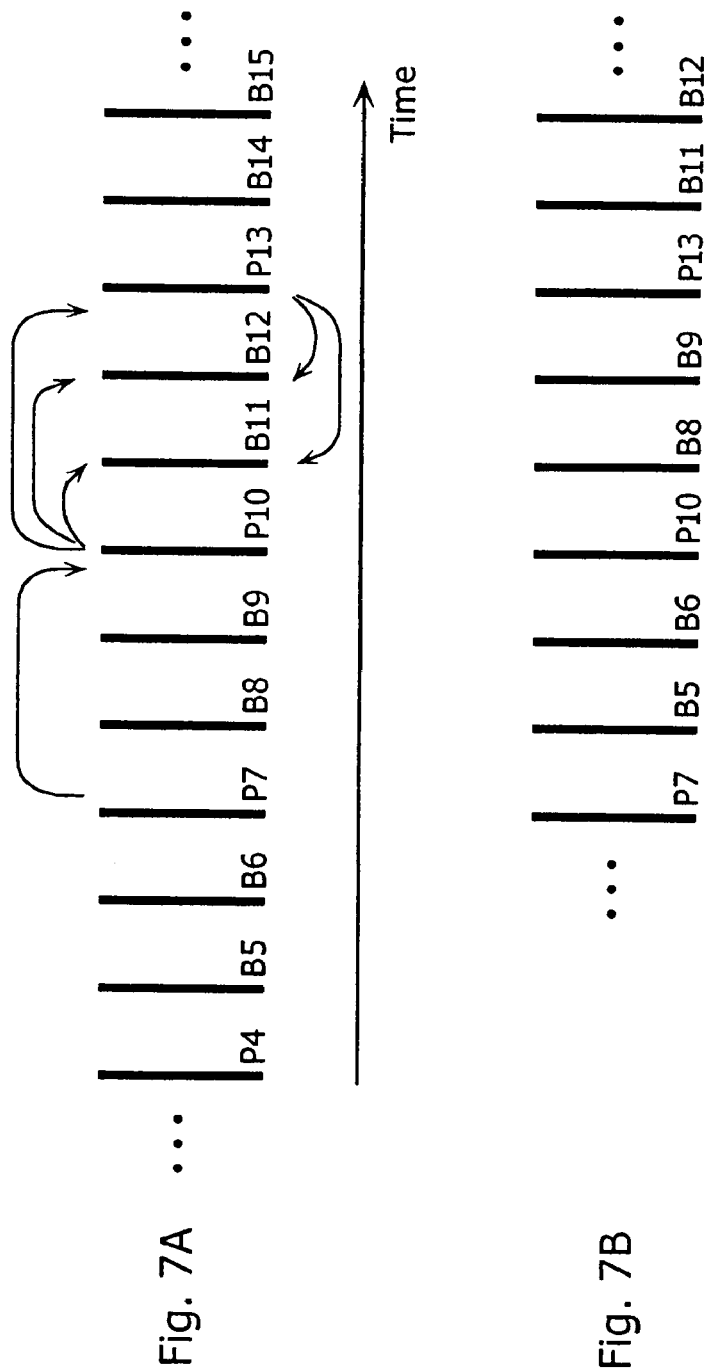
FIGS. 7A and 7B are diagrams showing how the pictures in a frame memory are inputted and outputted in the first embodiment.

FIG. 7A shows how the pictures are inputted in the frame memory 101.

In FIG. 7A, vertical lines show pictures, and an alphabet and a number at the lower right of each picture indicates a picture type (I, P or B) and a picture number in order of time. The pictures inputted to the frame memory 101 are reordered into coding order. The pictures are reordered into coding order based on the reference relations in inter picture prediction coding, that is, the pictures are reordered so that the pictures used as reference pictures are coded earlier than the pictures which refer to those reference pictures. For example, the reference relations of the pictures P7~P13 are shown by arrows in FIG. 7A. In FIG. 7A, the arrowheads indicate the pictures which refer to reference pictures, and the other ends of the arrows indicate the reference pictures. In this case, the pictures shown in FIG. 7A are reordered into those as shown in FIG. 7B.

FIG. 7B shows the pictures inputted as shown in FIG. 7A and reordered. The pictures reordered in the frame memory 101 are read out on a macroblock basis. In this case, a macroblock is horizontal 16×vertical 16 pixels in size.

The difference calculation unit 102 obtains image data of every macroblock from the frame memory 101 via the switch 111, and also obtains a motion compensation image from the mode selection unit 109. Then, the difference calculation unit 102 calculates the difference between the image data and the motion compensation image on a macroblock basis to generate a prediction error image for output.

The prediction error coding unit 103 performs coding processing including frequency transformation like discrete cosine transformation and quantization on the image data obtained from the frame memory 101 via the switch 112 and the prediction error image obtained by the difference calculation unit 102, so as to create coded data. For example, the frequency transformation and quantization are performed in a unit of horizontal 8×vertical 8 pixels. Then, the prediction error coding unit 103 outputs the coded data to the bit stream generation unit 104 and the prediction error decoding unit 105.

The bit stream generation unit 104 performs variable length coding on the coded data outputted from the prediction error coding unit 103, converts the data into that in a bit stream format for output, and further adds information on motion vectors inputted from the motion vector coding unit 117, information on a coding mode inputted from the mode selection unit 109, header information and others, so as to generate a bit stream.

The prediction error decoding unit 105 inversely quantizes the coded data outputted from the prediction error coding unit 103, and then performs inverse frequency transformation such as inverse discrete cosine transformation so as to decode it into a prediction error image.

The addition unit 106 adds the motion compensation image to the prediction error image obtained as a result of decoding, and outputs a decoded picture that is image data indicating an image of one picture which has been coded and decoded.

The frame memory 107 is a picture memory which holds, on a picture-by-picture basis, pictures used as reference pictures when coding other pictures, out of the decoded pictures outputted from the addition unit 106.

The motion vector estimation unit 108 estimates motion vectors of each block in a current macroblock to be coded, using the decoded pictures accumulated in the frame memory 107 as reference pictures. The estimated motion vectors are outputted to the mode selection unit 109.

The mode selection unit 109 determines a coding mode of the macroblock using the motion vectors estimated by the motion vector estimation unit 108. Here, the coding mode means a method for coding a macroblock. For example, when a current picture is a P-picture, the mode selection unit 109 determines a coding mode out of the following: intra picture coding, inter picture prediction coding using motion vectors, and skip mode (inter picture prediction coding in which no motion vector of a current block is coded because prediction coding is performed using a motion vector obtained from motion vectors of other blocks, and no coefficient value is coded because all the coefficient values are 0 as a result of the prediction error coding). Generally, a coding mode is determined so as to minimize a coding error using a predetermined bit amount.

The mode selection unit 109 outputs the determined coding mode to the bit stream generation unit 104, and outputs the motion vectors used for that coding mode to the motion vector coding unit 117, respectively. When the determined coding mode is inter picture prediction coding using motion vectors, the mode selection unit 109 further stores the motion vectors and the coding mode used for that inter picture prediction coding in the motion vector storage unit 116.

Also, the mode selection unit 109 performs motion compensation based on the determined coding mode and the motion vectors estimated by the motion vector estimation unit 108 so as to create a motion compensation image, and outputs the motion compensation image to the difference calculation unit 102 and the addition unit 106. However, if intra picture coding is selected, no motion compensation image is outputted. When selecting intra picture coding, the mode selection unit 109 further controls the switch 111 and the switch 112 to connect to a terminal "a" and a terminal "c" respectively, and when selecting inter picture prediction coding, it controls the switch 111 and the switch 112 to connect to a terminal "b" and a terminal "d" respectively. The above-mentioned motion compensation is performed on a block-by-block basis (8×8 pixels in this case).

The coding control unit 110 determines a picture type (I, P or B) used for coding an inputted picture, and controls the switches 113, 114 and 115 depending on the picture type. Here, a picture type is generally determined using a method for allocating a picture type periodically, for example.

The motion vector storage unit 116 obtains the motion vectors used for inter picture prediction coding and the coding mode from the mode selection unit 109, and stores them.

When the mode selection unit 109 selects inter picture prediction coding using motion vectors, the motion vector coding unit 117 codes a motion vector of a current block by the methods illustrated in FIGS. 3A-3D and FIG. 4. As described above, the motion vector coding unit 117 specifies three neighboring blocks of the current block, determines a predictive value based on the motion vectors of the neighboring blocks, and codes a difference between the predictive value and the motion vector of the current block to be coded.

When coding a motion vector of a current block, if a neighboring block is coded using motion vectors of other blocks, such as skip mode and direct mode, the motion vector coding unit 117 in the present embodiment does not consider the motion vector of the neighboring block to be 0 as the conventional art does, but treats a motion vector obtained from the motion vectors of the other blocks as the motion vector of the neighboring block when coding it.

Figure 8:
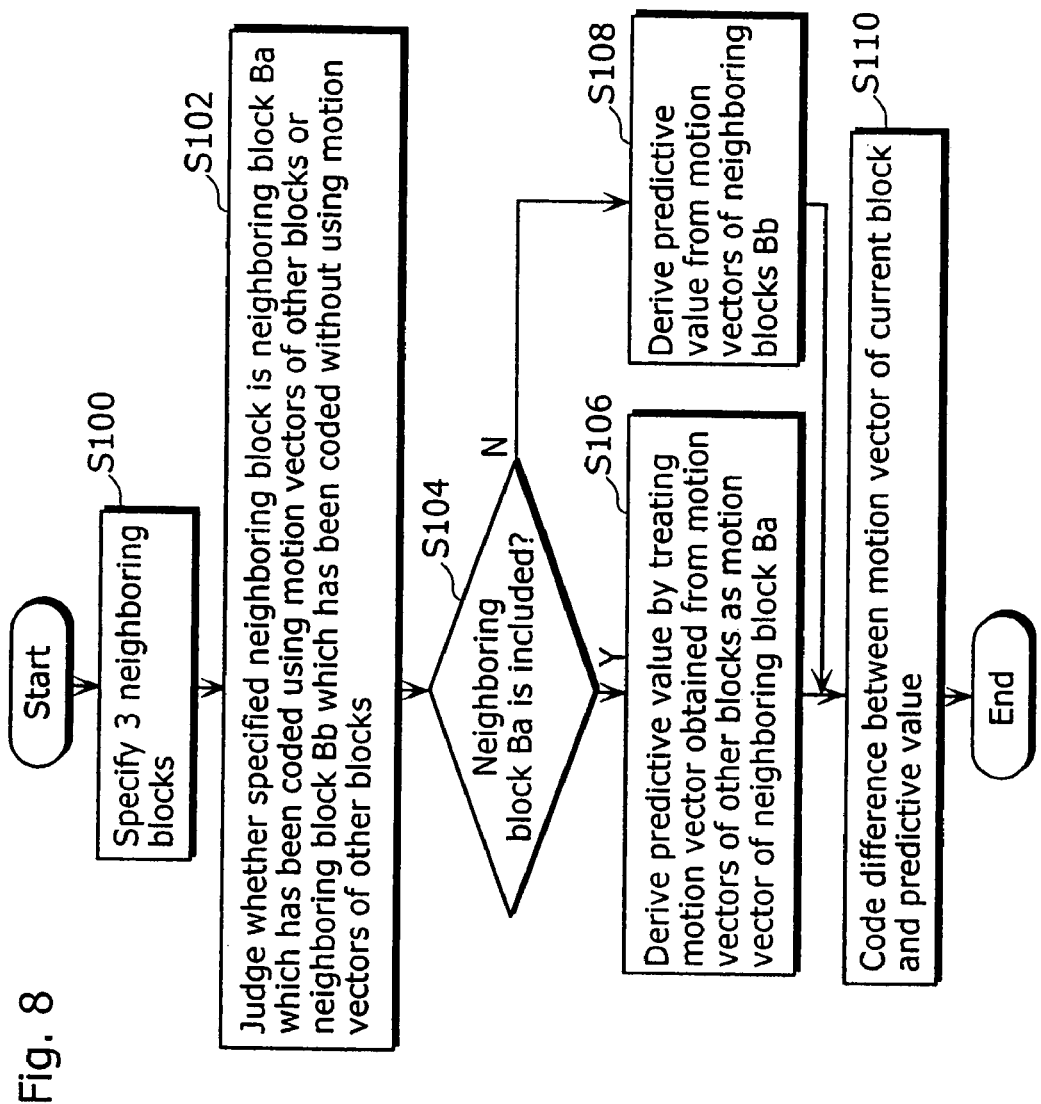
FIG. 8 is a flowchart showing an operation of a motion vector coding unit in the first embodiment.

FIG. 8 is a flowchart showing the general operation of the motion vector coding unit 117 in the present embodiment.

First, the motion vector coding unit 117 specifies three previously coded neighboring blocks of a current block (Step S100).

The motion vector coding unit 117 judges whether each of the specified neighboring blocks is a neighboring block Ba which has been coded using motion vectors of other blocks or a neighboring block Bb which has been coded without using motion vectors of other blocks (Step S102).

As a result, the motion vector coding unit 117 determines whether the specified three neighboring blocks include a neighboring block Ba or not (Step S104).

When it is judged in Step S104 that the neighboring block Ba is included (Y in Step S104), the motion vector coding unit 117 derives a predictive value from the motion vectors of the three neighboring blocks by treating a motion vector obtained from the motion vectors of the other blocks as a motion vector of the neighboring block Ba for coding it, as mentioned above (Step S106).

On the other hand, when it is judged in Step S104 that the neighboring block Ba is not included (N in Step s104), the motion vector coding unit 117 derives a predictive value from motion vectors obtained based on the motion estimation from respective three neighboring blocks Bb and the mode selection (Step S108).

Then, the motion vector coding unit 117 codes a difference between the motion vector of the current block and the predictive value derived in Steps S106 or S108 (Step S110). The motion vector coding unit 117 also outputs the motion vector coded as above to the bit stream generation unit 104.

Here, the above-mentioned coding processing by the moving picture coding apparatus 100 will be explained specifically by taking coding of a picture P13 and a picture B11 as shown in FIGS. 7A and 7B as an example.

(Coding of Picture P13)

Since the picture P13 is a P-picture, the moving picture coding apparatus 100 codes the picture 13 by inter picture prediction coding using another picture as a reference picture. In this case, the reference picture is a picture P10. This picture P10 has been already coded, and the decoded picture thereof is stored in the frame memory 107.

When coding a P-picture, the coding control unit 110 controls the switches 113, 114 and 115 to be ON. Therefore, macroblocks in the picture P13 which are read out from the frame memory 101 are obtained by the motion vector estimation unit 108, the mode selection unit 109 and the difference calculation unit 102.

The motion vector estimation unit 108 estimates the motion vector of each block in the macroblock using the decoded picture of the picture P10 stored in the frame memory 107 as a reference picture, and outputs the estimated motion vector to the mode selection unit 109.

The mode selection unit 109 determines a coding mode of the macroblock in the picture P13 using the motion vector estimated by the motion vector estimation unit 108. Since the picture P13 is a P-picture, the mode selection unit 109 determines, as mentioned above, a coding mode out of the following: intra picture coding, inter picture prediction coding using motion vectors, and skip mode (an inter picture prediction coding in which no motion vector of a current block is coded because prediction coding is performed using a motion vector obtained from motion vectors of other blocks, and no coefficient value is coded because all the coefficient values are 0 as a result of the prediction error coding).

When the mode selection unit 109 selects inter picture prediction coding using motion vectors, the motion vector coding unit 117 in the present embodiment codes the motion vector of the current block in the picture P13 by the method as illustrated in FIGS. 3A-3D. When a neighboring block of the current block is coded in skip mode, the motion vector coding unit 117 does not consider the motion vector of the neighboring block to be 0, but treats a motion vector obtained from other blocks for coding the neighboring block as a motion vector of that block.

A method of coding a motion vector of a current block used when a neighboring block is coded in skip mode will be explained.

Figure 9:
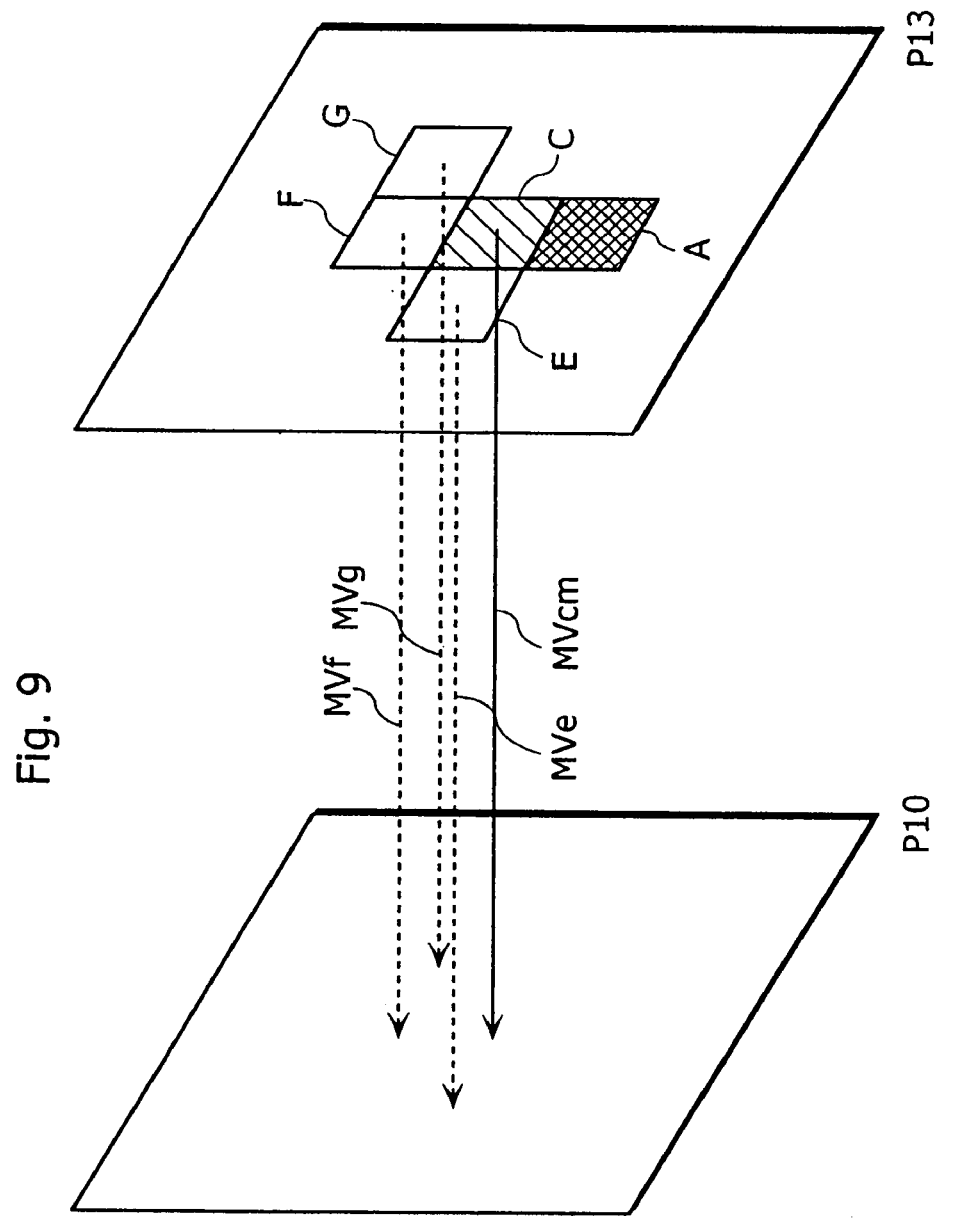
FIG. 9 is an illustration for explaining how to code a neighboring block in skip mode in the first embodiment.

FIG. 9 is an illustration for explaining how to code a neighboring block C in skip mode.

As shown in FIG. 9, when a neighboring block C in the picture P13 is coded in skip mode, a median of a motion vector MVe of a block E, a motion vector MVf of a block F and a motion vector MVg of a block G, which are located in the neighborhood of the neighboring block C, is calculated, and the neighboring block C is coded using a motion vector MVcm indicating the median. Here, a median of motion vectors is obtained by calculating medians of horizontal and vertical components of the motion vectors respectively, for example.

When coding the motion vector of the current block A as shown in FIG. 9, the motion vector coding unit 117 specifies the three neighboring blocks B, C and D of the current block A (as for the locations of the blocks B, C and D, see FIGS. 3A-3D and FIG. 4), and judges whether or not each of the neighboring blocks B, C and D is a block which has been coded using motion vectors of other blocks. As a result, when it is judged that only the neighboring block C is coded in skip mode, that is, coded using other blocks, the motion vector coding unit 117 treats the median (a motion vector MVcm) calculated from the motion vectors of the other blocks E, F and G for coding the neighboring block C as a motion vector of the neighboring block C, as mentioned above, and calculates the median of the motion vector MVcm and the motion vectors of the neighboring blocks B and D so as to consider it as a predictive value of the motion vector of the current block A. Then, the motion vector coding unit 117 codes a difference between the predictive value and the motion vector of the current block A.

The motion vector storage unit 116 stores coding modes of coded blocks. The motion vector coding unit 117 judges whether each of the neighboring blocks B, C and D is a block coded using motion vectors of other blocks or not based on the coding modes stored in the motion vector storage unit 116. The motion vector storage unit 116 further stores motion vectors of blocks which have been coded without using motion vectors of other blocks but using their own motion vectors estimated from reference pictures. To be more specific, the motion vector storage unit 116 stores the motion vectors MVe, MVf and MVg of the blocks E, F and G, and the motion vector coding unit 117 calculates the above-mentioned motion vector MVcm of the neighboring block C using these motion vectors stored in the motion vector storage unit 116 when coding the motion vector of the current block A. Note that as for a picture which has been coded using motion vectors of other blocks, a motion vector thereof which is obtained by calculating a median of the motion vectors of the other blocks may be stored in the motion vector storage unit 116 in advance. In this case, since the motion vector storage unit 116 stores the motion vector MVcm in advance, the motion vector coding unit 117 does not need to calculate the motion vector MVcm of the neighboring block C but can use the motion vector MVcm stored in the motion vector storage unit 116 directly as a motion vector of the neighboring block C, when coding the motion vector of the current block A.

On the other hand, a prediction error image indicating a difference between a current macroblock in the picture P13 and a motion compensation image is coded by the prediction error coding unit 103 and generated as coded data, and information on the motion vector coded as mentioned above is added to the coded data by the bit stream generation unit 104. However, a difference between a macroblock which has been coded in skip mode and a motion compensation image is 0, and information on the motion vector is not added to the coded data.

The remaining macroblocks in the picture P13 are coded in the same manner. After completing coding of all the macroblocks in the picture P13, coding of the picture B11 follows.

(Coding of Picture B11)

Since the picture B11 is a B-picture, the moving picture coding apparatus 100 codes the picture B11 by inter picture prediction coding using two other pictures as reference pictures. In this case, the reference pictures are the picture P10 located forward of the picture B11 and the picture P13 located backward of the picture B11. These pictures P10 and P13 have been already coded, and the decoded pictures thereof are stored in the frame memory 107.

When coding a B-picture, the coding control unit 110 controls the switch 113 to be ON and the switches 114 and 115 to be OFF. Therefore, macroblocks in the picture B11 which are read out from the frame memory 101 are obtained by the motion vector estimation unit 108, the mode selection unit 109 and the difference calculation unit 102.

The motion vector estimation unit 108 estimates the forward motion vector and the backward motion vector of each block in a macroblock using a decoded picture of the picture P10 stored in the frame memory 107 as a forward reference picture and a decoded picture of the picture P13 as a backward reference picture, and outputs the estimated forward and backward motion vectors to the mode selection unit 109.

The mode selection unit 109 determines a coding mode of the macroblock in the picture B11 using the forward and backward motion vectors estimated by the motion vector estimation unit 108. Since the picture B11 is a B-picture, the mode selection unit 109 determines a coding mode out of the following: intra picture coding, inter picture prediction coding using forward motion vectors, inter picture prediction coding using backward motion vectors, inter picture prediction coding using bi-directional motion vectors, and direct mode (inter picture prediction coding in which motion compensation is performed using a motion vector obtained from motion vectors of other blocks and no motion vector is coded), for example.

When the mode selection unit 109 selects inter picture prediction coding using motion vectors, the motion vector coding unit 117 in the present embodiment codes the motion vectors of the current block in the picture B11 by the method as illustrated in FIGS. 3A-3D.

More specifically, when the mode selection unit 109 selects inter picture prediction coding using bi-directional motion vectors, the motion vector coding unit 117 codes the motion vectors of the current block in the following manner.

Figure 10:
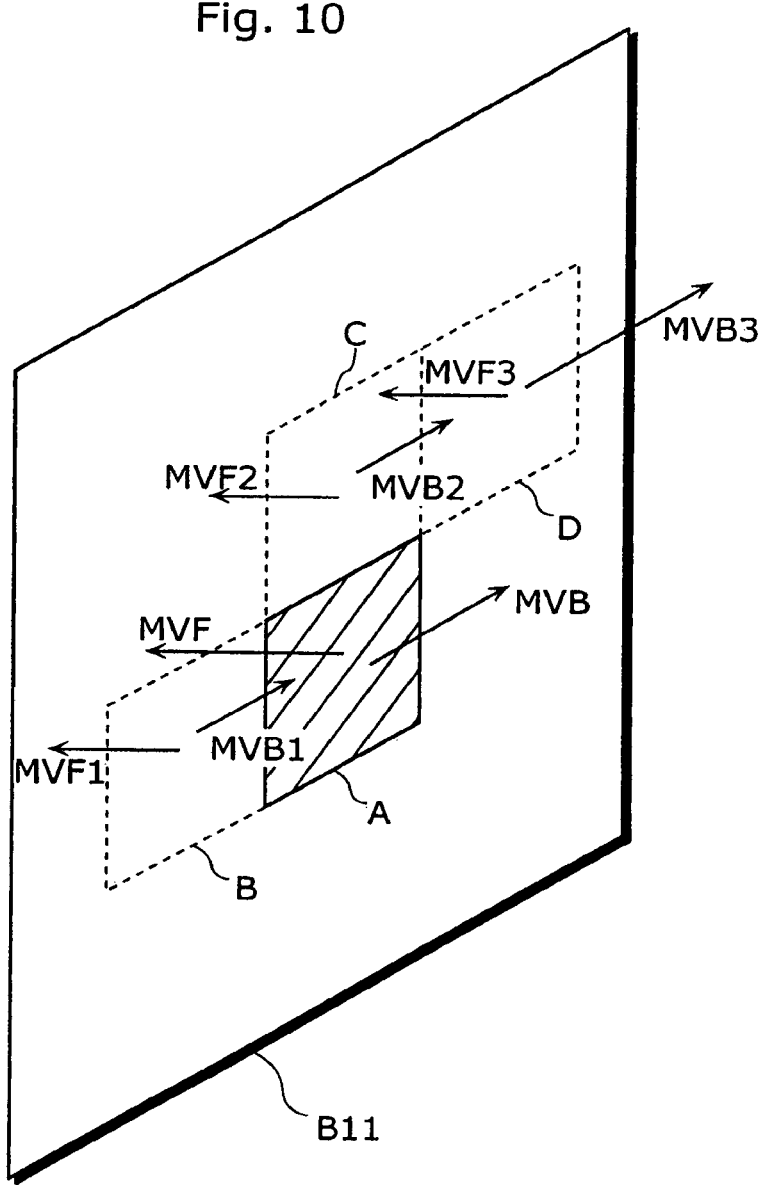
FIG. 10 is an illustration for explaining inter picture prediction coding using bi-directional motion vectors in the first embodiment.

FIG. 10 is an illustration for explaining inter picture prediction coding using bi-directional motion vectors.

When coding motion vectors of a current block A, the motion vector coding unit 117 codes a forward motion vector MVF and a backward motion vector MVB.

To be more specific, the motion vector coding unit 117 considers a median of forward motion vectors MVF1, MVF2 and MVF3 of the neighboring blocks B, C and D to be a predictive value of the forward motion vector MVF, and codes a difference between the forward motion vector MVF and the predictive value thereof. The motion vector coding unit 117 also considers a median of backward motion vectors MVB1, MVB2 and MVB3 of the neighboring blocks B, C and D to be a predictive value of the backward motion vector MVB, and codes a difference between the backward motion vector MVB and the predictive value thereof. Here, the median of the motion vectors is obtained by calculating medians of horizontal and vertical components of the motion vectors respectively, for example.

When coding motion vectors of a current block in a B-picture, if a neighboring block has been coded in direct mode, the motion vector coding unit 117 in the present embodiment does not consider the motion vectors of the neighboring block to be 0, but considers motion vectors obtained from other blocks as motion vectors of the neighboring block. There are two types of direct modes: temporal direct mode and spatial direct mode.

First, how to code motion vectors of a current block when a neighboring block is coded in temporal direct mode will be explained.

Figure 11:
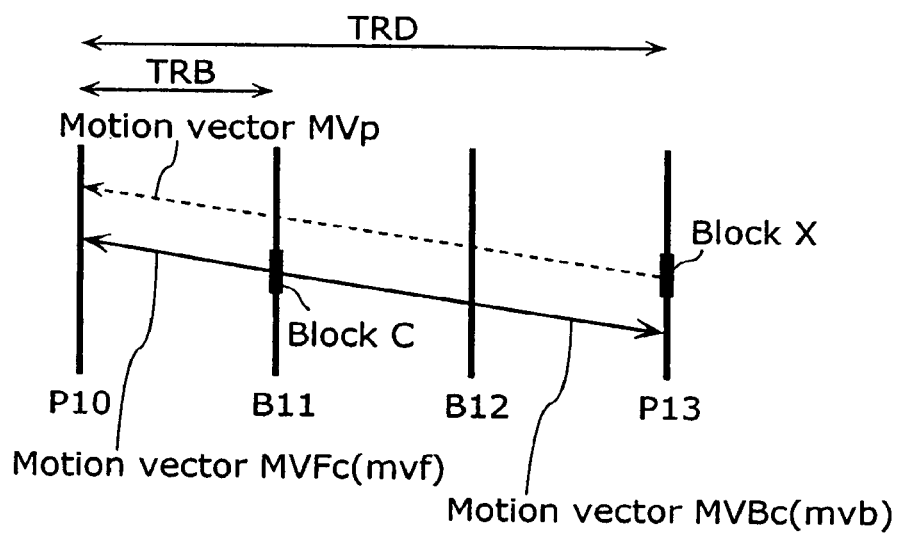
FIG. 11 is an illustration for explaining how to code a neighboring block in temporal direct mode in the first embodiment.

FIG. 11 is an illustration for explaining how to code the neighboring block in temporal direct mode.

As shown in FIG. 11, when the neighboring block C in the picture B11 is coded in direct mode, a motion vector MVp of a block X, which is co-located with the neighboring block C, in the picture P13 that is a just previously coded backward reference picture, is used. The motion vector MVp is a motion vector used for coding the block X, and is stored in the motion vector storage unit 116. This motion vector MVp refers to the picture P10. The neighboring block C is coded by bi-directional prediction from the reference pictures, the picture P10 and the picture P13, using motion vectors parallel to the motion vector MVp. In this case, the motion vectors used for coding the neighboring block C are a motion vector MVFc for the picture P10 and a motion vector MVBc for the picture P13.

In this case where the forward motion vector MVFc is mvf, the backward motion vector MVBc is mvb, the motion vector MVp is mvp, the temporal distance between the backward reference picture (picture P13) for the current picture (picture B11) and the reference picture (picture P10) pointed by the block in the backward reference picture is TRD, and the temporal distance between the current picture (picture B11) and the reference picture (picture P10) pointed by the block in the backward reference picture is TRB, mvf and mvb are respectively calculated by Equation 1 and Equation 2.

$$mvf = mvp \times TRB/TRD \qquad \text{Equation 1}$$

$$mvb = (TRB - TRD) \times mvp/TRD \qquad \text{Equation 2}$$

where mvf and mvb respectively represent horizontal components and vertical components of the motion vectors. And the plus values indicate the direction of the motion vector MVp, and the minus values indicate the direction opposite to that of the motion vector MVp.

The neighboring block C is coded using the motion vectors MVFc and MVBc obtained as mentioned above.

When coding the motion vectors MVF and MVB of the current block A as shown in FIG. 10, the motion vector coding unit 117 specifies the three neighboring blocks B, C and D of the current block A, and judges whether or not each of the neighboring blocks B, C and D is a block which has been coded using a motion vector of another block. As a result, when it is judged that only the neighboring block C is coded in temporal direct mode, that is, coded using the motion vector of the other block, the motion vector coding unit 117 treats the motion vectors MVFc and MVBc calculated from the motion vector MVp of the block X that is the other block for coding the neighboring block C as motion vectors of the neighboring block C, and calculates the medians of the motion vectors MVFc and MVBc and the motion vectors of the neighboring blocks B and D so as to derive predictive values of the motion vectors of the current block A. A forward predictive value and a backward predictive value are derived separately. Then, the motion vector coding unit 117 codes differences between the predictive values and the motion vectors MVF and MVB of the current block A, respectively.

The motion vector storage unit 116 stores coding modes of coded blocks, and based on the coding modes stored in this motion vector storage unit 116, the motion vector coding unit 117 judges whether or not each of the neighboring blocks B, C and D has been coded using motion vectors of other blocks. The motion vector storage unit 116 further stores motion vectors of blocks which have been coded without using motion vectors of other blocks but using their own motion vectors estimated from reference pictures. In other words, when coding the motion vectors of the current block A, the motion vector coding unit 117 uses the motion vectors stored in the motion vector storage unit 116 as they are for the neighboring blocks B and D, but for the neighboring block C, it reads out the motion vector MVp of the block X stored in the motion vector storage unit 116 to calculate the motion vectors MVFc and MVBc. Note that the motion vector storage unit 116 may store in advance motion vectors calculated from motion vectors of other blocks in order to code a block which has been coded using the motion vectors of the other blocks. In this case, the motion vector storage unit 116 stores in advance the motion vectors MVFc and MVBc. Therefore, when coding the motion vectors of the current block A, the motion vector coding unit 117 does not need to read out the motion vector MVp of the block X so as to calculate the motion vectors MVFc and MVBc of the neighboring block C using Equation 1 and Equation 2, but can use the motion vectors MVFc and MVBc stored in the motion vector storage unit 116 directly as the motion vectors of the neighboring block C.

Next, a method for coding motion vectors of a current block in a case where a neighboring block is coded in spatial direct mode will be explained.

Figure 12:
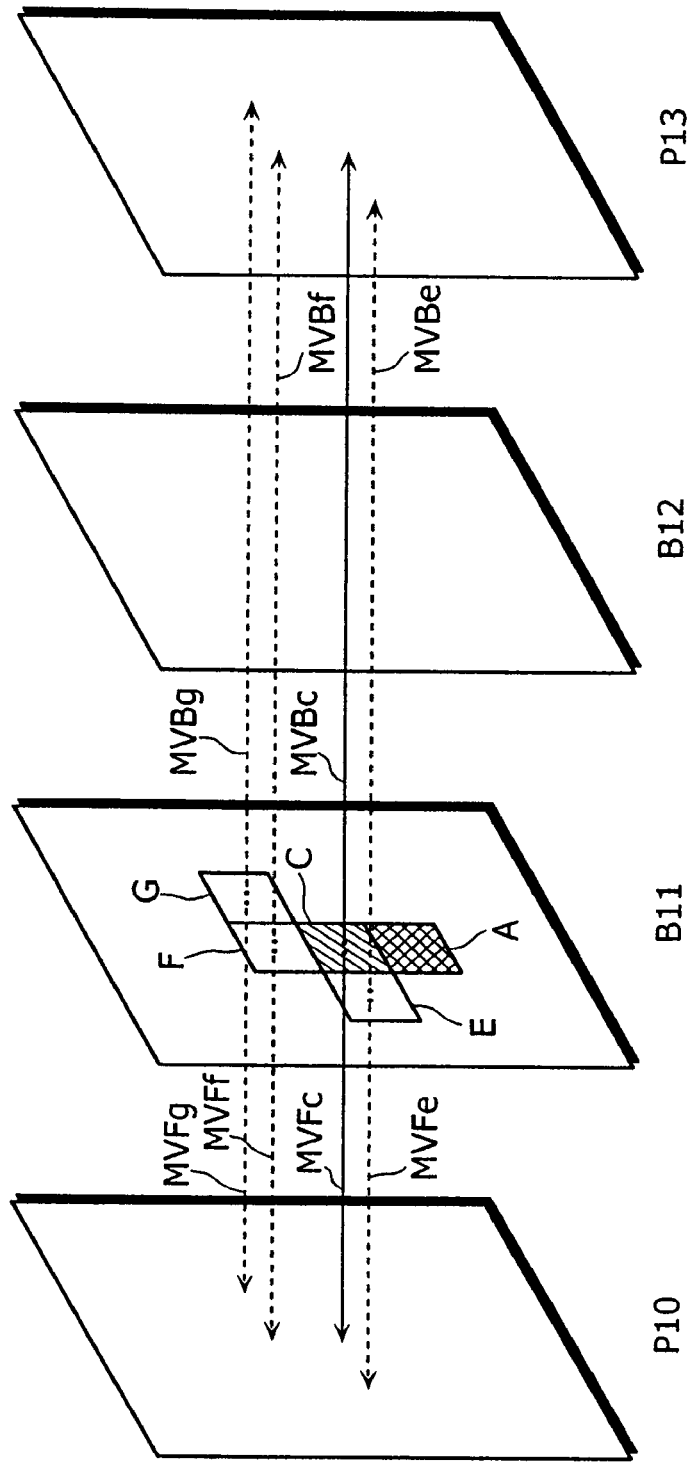
FIG. 12 is an illustration for explaining how to code a neighboring block in spatial direct mode in the first embodiment.

FIG. 12 is an illustration for explaining how to code a neighboring block in spatial direct mode.

As shown in FIG. 12, when a neighboring block C of the picture B11 is coded in spatial direct mode, it is coded using motion vectors MVFc and MVBc calculated based on medians in the forward and backward directions respectively which are obtained from the motion vectors MVFe and MVBe of the block E, the motion vectors MVFf and MVBf of the block F and the motion vectors MVFg and MVBg of the block G, where the blocks E, F and G are located in the neighborhood of the neighboring block C.

When coding the motion vectors MVF and MVB of the current block A as shown in FIG. 10, the motion vector coding unit 117 specifies the three neighboring blocks B, C and D in the neighborhood of the current block A, and judges whether each of the neighboring blocks B, C and D is a block which has been coded using motion vectors of other blocks or not. As a result, when the motion vector coding unit 117 judges that only the neighboring block C has been coded in spatial direct mode, that is, using motion vectors of other blocks, it treats the motion vectors MVFc and MVBc calculated from the blocks E, F and G which are the other blocks used for coding the neighboring block C as the motion vectors of the neighboring block C, calculates the medians of the motion vectors MVFc and MVBc and the motion vectors of the neighboring blocks B and D, and thus derives predictive values of the motion vectors of the current block A, as shown in FIG. 12. Then, the motion vector coding unit 117 codes differences between the predictive values and the motion vectors MVF and MVB of the current block A.

The motion vector storage unit 116 stores motion vectors of blocks which have been coded without using motion vectors of other blocks but using their own motion vectors estimated from reference pictures. In other words, it stores two motion vectors in the forward and backward directions for each of the blocks E, F and G. When coding the motion vectors of the current block A, the motion vector coding unit 117 calculates the motion vectors MVFc and MVBc of the neighboring block C using these motion vectors stored in the motion vector storage unit 116. Note that the motion vector storage unit 116 may store in advance two motion vectors in the forward and backward directions which are calculated based on medians obtained from motion vectors of other blocks in order to code a block which has been coded using the motion vectors of the other blocks. In this case, the motion vector storage unit 116 stores in advance the motion vectors MVFc and MVBc. Therefore, when coding the motion vectors of the current block A, the motion vector coding unit 117 does not need to calculate the motion vectors MVFc and MVBc of the neighboring block C, but can use the motion vectors MVFc and MVBc stored in the motion vector storage unit 116 directly as the motion vectors of the neighboring block C.

As described above, when the neighboring block C is coded in the above temporal direct mode, the motion vectors of the backward reference picture (the picture P13 in the above case) of the current picture needs to be stored in the motion vector storage unit 116, but when the neighboring block C is coded in spatial direct mode, the storage thereof can be omitted.

Here, when coding motion vectors of a current block, the moving picture coding apparatus 100 performs an exceptional processing if a neighboring block of the current block is not inter picture prediction coded, as mentioned above, but intra picture coded.

For example, when there exists one block which has been intra picture coded in the three neighboring blocks, the motion vector coding unit 117 of the moving picture coding apparatus 100 performs processing considering the motion vectors of the block to be 0. When there exist two neighboring blocks which have been intra picture coded, the motion vector coding unit 117 uses the motion vectors of the remaining one neighboring block as predictive values of motion vectors of a current block. Further, when all of the three neighboring blocks have been intra picture coded, the motion vector coding unit 117 performs coding processing of the motion vectors of the current block considering the predictive values thereof to be 0.

On the other hand, the prediction error image indicating a difference between a current macroblock in the picture B11 and the motion compensation image has been coded by the prediction error coding unit 103 and generated as coded data, and information on the motion vectors which have been coded as mentioned above is added to the coded data by the bit stream generation unit 104. However, information on motion vectors of a macroblock which has been coded in direct mode is not added to the coded data.

Coding processing of the remaining macroblocks in the picture B11 is performed in the same manner. After the processing is completed for all the macroblocks in the picture B11, the coding processing of the picture B12 follows.

As described above, according to the motion vector coding method of the present invention, a motion vector of each current block is coded using a predictive value derived from motion vectors of the previously coded neighboring blocks and the motion vector of the current block. If any of the neighboring blocks has been coded using a motion vector calculated from motion vectors of other blocks, for example, in skip mode or direct mode, a predictive value is derived using, as a motion vector of the neighboring block, the motion vector calculated from the motion vectors of the other blocks for coding that neighboring block.

Accordingly, when a motion vector of a current block is coded using a predictive value derived from a motion vector of a neighboring block, if the neighboring block is coded using motion vectors of other blocks, the motion vector of the neighboring block is not considered as 0 like the conventional art, but the motion vector calculated from the motion vectors of the other blocks is used as the motion vector of the neighboring block. As a result, accuracy of the above predictive value is improved, and thus efficiency of coding motion vectors can be improved.

Note that in the present embodiment, a case has been explained where a macroblock is coded in every horizontal 16×vertical 16 pixels, motion compensation is performed in every block of horizontal 8×vertical 8 pixels, and a block prediction error image is coded in every horizontal 8×vertical 8 pixels, but this processing may be performed in other units of pixels.

Also, in the present embodiment, a case has been explained where a median calculated from motion vectors of previously coded three neighboring blocks is used as a predictive value for coding a motion vector, but any other number of neighboring blocks other than three may be applied, and the predictive value may be determined by any other method. For example, a motion vector of an immediately left block may be used as a predictive value, or an average, instead of a median, may be used.

Also, in the present embodiment, locations of neighboring blocks for coding a motion vector has been explained using FIGS. 3A-3D and FIG. 4, but any other locations may be applied.

Also, in the present embodiment, a method for coding a current block using motion vectors of other blocks has been explained by taking skip mode and temporal and spatial direct modes as examples, but any other method may be used.

Also, in the present embodiment, a case has been explained where a difference between a motion vector of a current block and a predictive value obtained from motion vectors of neighboring blocks so as to code the motion vector, but any other method other than obtaining of a difference may be used to code the motion vector.

Also, in the present embodiment, a case has been explained where when a neighboring block is coded in spatial direct mode, a median of motion vectors of previously coded three blocks in the neighborhood of the neighboring block is calculated and is treated as a motion vector of the neighboring block, but any other number of blocks other than three may be used, and any other method may be used to determine the motion vector. For example, a motion vector of an immediately left block may be used as a motion vector of a neighboring block, or an average, instead of a median, may be used.

Also, in the present embodiment, when a block in a B-picture is coded in spatial direct mode, two motion vectors of the block in the forward and backward directions are calculated, but two motion vectors in the forward direction only or two motion vectors in the backward direction only may be calculated. In this case, the B-picture refers to two pictures in the forward direction only or two pictures in the backward direction.

Also, in the present embodiment, a case has been explained where one predetermined picture is referred to in coding a P-picture (a picture P10 is referred to in coding a picture P13, for example) and two predetermined pictures are referred to in coding a B-picture (pictures P10 and P13 are referred to in coding a picture B11), but these P-picture and B-picture may be coded by selecting reference pictures for every macroblock or block from among a plurality of pictures. In such a case, a predictive value of a motion vector can be generated in the manner as shown in FIG. 13.

Figure 13:
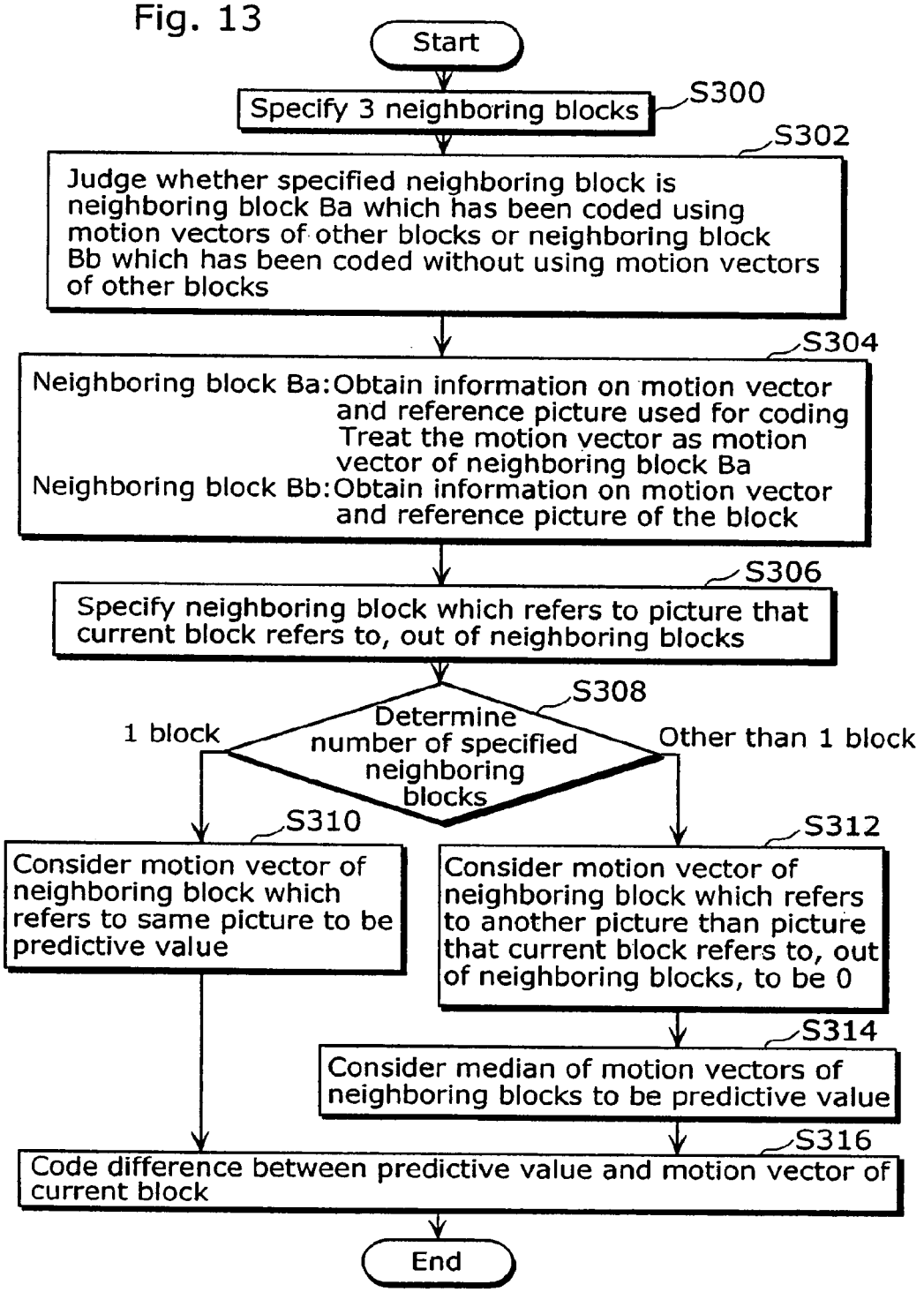
FIG. 13 is a flowchart showing another operation of the motion vector coding unit in the first embodiment.

FIG. 13 is a flowchart showing an operation the motion vector coding unit 117 conducts in deriving a predictive value of a motion vector of a current block to code the motion vector, when reference pictures are selected for every block.

First, the motion vector coding unit 117 specifies previously coded three neighboring blocks of a current block (Step S300).

Then, the motion vector coding unit 117 judges whether each of the specified neighboring blocks is a neighboring block Ba which has been coded using motion vectors of other blocks or a neighboring block Bb which has been coded without using motion vectors of other blocks (Step S302).

Here, as for the neighboring block Ba, the motion vector coding unit 117 obtains information indicating motion vectors used for coding the block Ba and reference pictures for the neighboring block Ba, and treats those motion vectors used for coding the block Ba as motion vectors thereof. As for the neighboring block Bb, the motion vector coding unit 117 obtains information indicating motion vectors of the neighboring block Bb and reference pictures for the neighboring block Bb (Step S304).

Next, the motion vector coding unit 117 specifies, out of the three neighboring blocks, a neighboring block which refers to the picture that a current block refers to based on the information obtained in Step S304 (Step S306), and determines the number of the specified neighboring blocks (Step S308).

Then, if the number of the neighboring blocks judged in Step S308 is 1, the motion vector coding unit 117 considers the motion vector of the neighboring block which refers to the same picture to be a predictive value of the motion vector MV of the current block (Step S310).

If the number of the neighboring blocks judged in Step S308 is not 1, the motion vector coding unit 117 considers the motion vectors of the neighboring blocks which refer to another picture other than the current block refers to, out of the three neighboring blocks, to be 0 (Step S312), and considers a median of the motion vectors of the three neighboring blocks to be a predictive value of the motion vector MV of the current block (Step S314).

Using the predictive value derived in Step S310 or Step S314 as mentioned above, the motion vector coding unit 117 calculates a difference between the predictive value and the motion vector MV of the current block, and codes the difference (Step S316).

Also, when a motion vector is coded using a motion vector of a spatially adjacent block as a predictive value, an amount of motion vectors of 1 macroblock line (a portion of 1 macroblock high and a screen wide) needs to be stored in the motion vector storage unit 116 for coding the motion vector, if the motion vectors which have been actually used for motion compensation in skip mode or direct mode are stored in the motion vector storage unit 116. This applies to the case where the motion vectors which have been actually used for motion compensation in skip mode or direct mode are stored in the motion vector storage unit 116. That is why when the neighboring blocks explained in connection with FIGS. 3A-3D and FIG. 4 of the present embodiment are used, there are past 1 macroblock slices of blocks which are referred to as neighboring blocks for coding the motion vector, with the current macroblock as a starting point.

Second Embodiment

A moving picture decoding apparatus 700 in the second embodiment of the present invention will be explained with reference to the figures.

Figure 14:
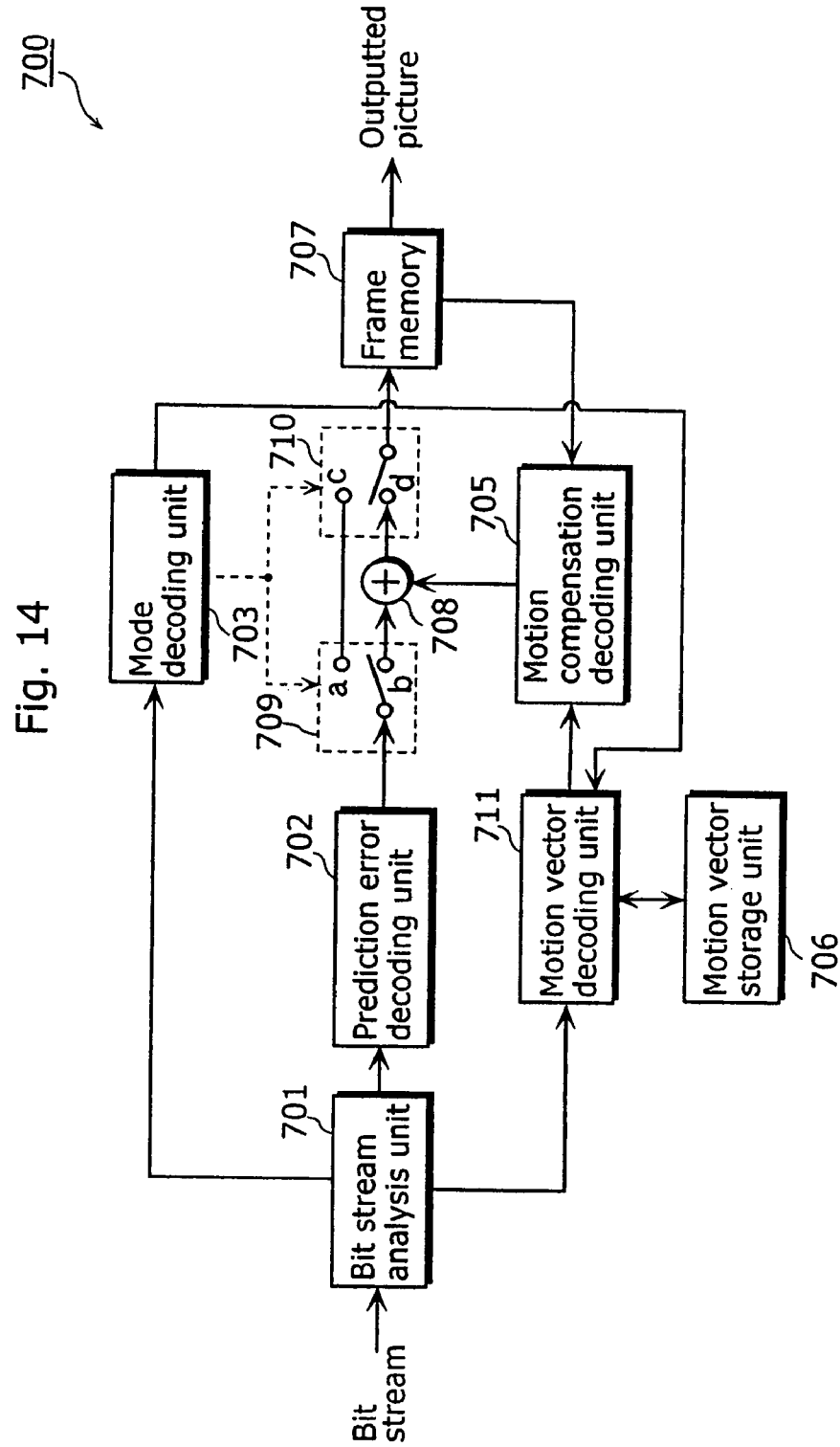
FIG. 14 is a block diagram showing a structure of a moving picture decoding apparatus in a second embodiment of the present invention.

FIG. 14 is a block diagram showing the structure of the moving picture decoding apparatus 700 in the second embodiment of the present invention.

The moving picture decoding apparatus 700 as shown in FIG. 14 decodes moving pictures coded by the moving picture coding apparatus 100 in the first embodiment, and includes a bit stream analysis unit 701, a prediction error decoding unit 702, a mode decoding unit 703, a motion compensation decoding unit 705, a motion vector storage unit 706, a frame memory 707, an addition unit 708, switches 709 and 710, and a motion vector decoding unit 711.

The bit stream analysis unit 701 extracts various data from the inputted bit stream. Here, various data includes information on coding mode, information on motion vectors, and so on. The extracted coding mode information is outputted to the mode decoding unit 703. The extracted motion vector information is outputted to the motion vector decoding unit 711. Further, the extracted coded prediction error data is outputted to the prediction error decoding unit 702.

The prediction error decoding unit 702 decodes the inputted coded prediction error data to generate a prediction error image. The generated prediction error image is outputted to the switch 709. When the switch 709 is connected to the terminal "b", the prediction error image is outputted to the addition unit 708.

The mode decoding unit 703 controls the switch 709 and the switch 710 with reference to the coding mode information extracted from the bit stream. If the coding mode is intra picture coding, the mode decoding unit 703 controls the switches 709 and 710 to connect to the terminal "a" and the terminal "c", respectively, and if the coding mode is inter picture coding, it controls the switches 709 and 710 to connect to the terminal "b" and the terminal "d", respectively. The mode decoding unit 703 further outputs the coding mode information to the motion vector decoding unit 711.

The motion vector decoding unit 711 decodes the motion vector information outputted from the bit stream analysis unit 701.

To be more specific, when the coding mode information indicates inter picture prediction coding using motion vectors, the motion vector decoding unit 711 derives a predictive value for a current block to be decoded using the motion vectors of previously decoded neighboring blocks, in the same manner as described in connection with FIGS. 3A-3D and FIG. 4. For example, as shown in FIGS. 3A-3D, the motion vector decoding unit 711 derives a predictive value for a current block A from the motion vector MVb of the neighboring block B, the motion vector MVc of the neighboring block C and the motion vector MVd of the neighboring block D. Here, the predictive value is calculated based on a median calculated from each of the horizontal components and vertical components of the three previously decoded motion vectors MVb, MVc and MVd. Then, the motion vector decoding unit 711 adds the predictive value to the difference that is the motion vector information outputted from the bit stream analysis unit 701 so as to determine the motion vector MV of the current block A. When the coding mode information is any of the above-mentioned skip mode, temporal direct mode, and spatial direct mode, the motion vector decoding unit 711 determines the motion vector using only the motion vectors of the previously decoded neighboring blocks.

FIG. 15 is a flowchart showing the general operation of the motion vector decoding unit 711 in the present embodiment.

First, the motion vector decoding unit 711 specifies previously decoded three neighboring blocks of a current block to be decoded (Step S200).

Then, the motion vector decoding unit 711 judges whether each of the specified neighboring blocks is a neighboring block which has been coded using motion vectors of other blocks or a neighboring block Bb which has been coded without using motion vectors of other blocks (Step S202).

As a result, the motion vector decoding unit 711 determines whether or not a neighboring block Ba is included in the specified three neighboring blocks (Step S204).

When it is judged in Step S204 that a neighboring block Ba is included (Y in Step S204), the motion vector decoding unit 711 derives a predictive value from the motion vectors of the three neighboring blocks by treating a motion vector calculated from motion vectors of other blocks for decoding the neighboring block Ba as a motion vector of the neighboring block Ba, as mentioned above (Step S206).

On the other hand, when it is judged in Step S206 that a neighboring block Ba is not included (N in Step S204), the motion vector decoding unit 711 derives a predictive value from the motion vectors obtained respectively based on the estimation results of the three neighboring blocks Bb (Step S208).

Then, the motion vector decoding unit 711 adds the predictive value derived in Step S206 or S208 to the difference that is the motion vector information outputted from the bit stream analysis unit 701, so as to decode the coded motion vector of the current block (Step S210). The motion vector decoding unit 711 also outputs the decoded motion vector to the motion compensation decoding unit 705.

The motion vector storage unit 706 stores the motion vector decoded in the motion vector decoding unit 711 and the coding mode obtained in the mode decoding unit 703.

The motion compensation decoding unit 705 obtains a motion compensation image of every macroblock from the frame memory 707 based on the motion vector decoded in the motion vector decoding unit 711.

The addition unit 708 adds the inputted prediction error image and the motion compensation image to generate the decoded image, and outputs the generated decoded image to the frame memory 707.

The frame memory 707 stores the decoded image generated by the addition unit 708 on every picture basis.

The operation of this moving picture decoding apparatus 700, particularly the general operation thereof, will be explained first.

FIGS. 16A and 16B are illustrations for explaining input to and output from the moving picture decoding apparatus 700.

As shown in FIG. 16A, the moving picture decoding apparatus 700 obtains the bit stream outputted from the moving picture coding apparatus 100 in the first embodiment in output order, and decodes the pictures included in the bit stream in sequence. Then, as shown in FIG. 16B, the moving picture decoding apparatus 700 reorders the decoded pictures in display order for output.

The decoding processing performed by the above moving picture decoding apparatus 700 will be explained below by taking decoding of the picture P13 and the picture B11 as shown in FIGS. 16A and 16B as a specific example.

(Decoding of Picture P13)

First, the bit stream analysis unit 701 of the moving picture decoding apparatus 700 obtains the bit stream regarding the picture P13, and extracts the mode selection information and the motion vector information and the coded prediction error data from the bit stream.

The mode decoding unit 703 controls the switches 709 and 710 with reference to the mode selection information extracted from the bit stream of the picture P13.

A case where the mode selection information indicates inter picture prediction coding will be explained below.

The motion vector decoding unit 711 performs the above decoding processing on the motion vector information extracted from the bit stream of the picture P13 on a block-by-block basis based on the mode selection information indicating inter picture prediction coding outputted from the mode decoding unit 703.

Here, when decoding the motion vector of the current block in the picture P13, the motion vector decoding unit 711 specifies previously decoded three neighboring blocks of the current block, and judges whether each of these neighboring blocks has been coded using motion vectors of other blocks or not. When any of the neighboring blocks is a block which has been coded using motion vectors of other blocks, namely, in skip mode, the motion vector decoding unit 711 treats a motion vector calculated from the motion vectors of the other blocks for decoding the neighboring block as a motion vector of the neighboring block, in the same manner as the motion vector coding unit 117 in the first embodiment does. To be more specific, the motion vector decoding unit 711 calculates the median of the motion vectors of the previously decoded three blocks in the neighborhood of that neighboring block, and treats it as a motion vector of the neighboring block.

Also, the motion vector storage unit 706 stores the mode selection information outputted from the mode decoding unit 703, and the motion vector decoding unit 711 judges whether or not each of the neighboring blocks is a block which has been coded using motion vectors of other blocks based on the mode selection information stored in the motion vector storage unit 706. The motion vector storage unit 706 further stores the motion vectors of the other blocks used for decoding the neighboring block. To be more specific, the motion vector storage unit 706 stores the motion vectors of the three blocks in the neighborhood of the neighboring block which has been coded in skip mode. When decoding the motion vector of the current block, the motion vector decoding unit 711 calculates a median from the motion vectors of the above three blocks stored in the motion vector storage unit 706. Note that the motion vector storage unit 706 may store in advance a motion vector of a block which has been coded using motion vectors of other blocks, by calculating a median of the motion vectors for decoding the block. In this case, when decoding the motion vector of the current block, the motion vector decoding unit 711 does not need to obtain the motion vector of the neighboring block which has been coded in skip mode, but can use the motion vector stored in the motion vector storage unit 706 directly as a motion vector of the neighboring block.

On the other hand, the coded prediction error data of the current macroblock in the picture P13 is decoded in the prediction error decoding unit 702 and generated as a prediction error image, and the switches 709 and 710 are connected to the addition unit 708. Therefore, the motion compensation image generated based on the motion vector decoded in the motion vector decoding unit 711 is added to the prediction error image and outputted to the frame memory 707.

Also, when decoding a motion vector of a P-picture, the motion vector decoding unit 711 stores its motion vector and a coding mode obtained from the mode decoding unit 703 in the motion vector storage unit 706 for decoding the following pictures and blocks.

The remaining macroblocks in the picture P13 are decoded in sequence. After decoding of all of the macroblocks in the picture P13 is completed, decoding of the picture B11 follows.

(Decoding of Picture B11)

First, the bit stream analysis unit 701 of the moving picture decoding apparatus 700 obtains the bit stream of the picture B11, and extracts the mode selection information and the motion vector information and the coded prediction error data from the bit stream.

The mode decoding unit 703 controls the switches 709 and 710 with reference to the mode selection information extracted from the bit stream of the picture B11.

A case where the mode selection information indicates inter picture prediction coding will be explained below.

The motion vector decoding unit 711 performs the above decoding processing on the motion vector information extracted from the bit stream of the picture B11 on a block-by-block basis based on the mode selection information indicating inter picture prediction coding outputted from the mode decoding unit 703.

When decoding a motion vector of a current block in the picture B11, the motion vector decoding unit 711 specifies previously decoded three neighboring blocks of the current block, and judges whether or not each of these neighboring blocks has been coded using motion vectors of other blocks. When any of the neighboring blocks is a block which has been coded using motion vectors of other blocks, namely, in temporal or spatial direct mode, the motion vector decoding unit 711 treats a motion vector obtained using the motion vectors of the other blocks for decoding the neighboring block as a motion vector thereof, in the same manner as the motion vector coding unit 117 in the first embodiment does.

More specifically, when the neighboring block has been coded in temporal direct mode, the motion vector decoding unit 711 reads out from the motion vector storage unit 706 a motion vector of a block, which is co-located with a neighboring block which has been coded in direct mode, in a just previously decoded reference picture (picture P13). For example, as shown in FIG. 11, if the neighboring block C has been coded in temporal direct mode, the motion vector decoding unit 711 reads out the decoded motion vector of the block X in the picture P13 from the motion vector storage unit 706. Then, the motion vector decoding unit 711 calculates a forward motion vector MVFc and a backward motion vector MVBc used for coding the neighboring block C using Equation 1 and Equation 2, and uses these motion vectors MVFc and MVBc as motion vectors of the neighboring block C.

In the above case, the motion vector decoding unit 711 reads out from the motion vector storage unit 706 the motion vector MVp of the block X in the picture P13 which is co-located with the neighboring block C which has been coded in direct mode. However, as for a block which has been coded using motion vectors of other blocks, the motion vector storage unit 706 may store the motion vector of the block calculated from the motion vectors of the other blocks for decoding the block. In this case, the motion vector storage unit 706 stores the motion vectors MVFc and MVBc in advance. Therefore, when decoding the motion vector of the current block A, the motion vector decoding unit 711 does not need to calculate the motion vectors MVFc and MVBc for the neighboring block C by reading out the motion vector MVp of the block X and using Equation 1 and Equation 2, but can use the motion vectors MVFc and MVBc stored in the motion vector storage unit 706 directly as motion vectors of the neighboring block C.

On the other hand, when a neighboring block has been coded in spatial direct mode, the motion vector decoding unit 711 treats motion vectors calculated using motion vectors of other blocks in the neighborhood of the neighboring block as motion vectors thereof. For example, in the situation as shown in FIG. 12, the motion vector decoding unit 711 calculates medians from the motion vectors of the previously decoded three blocks E, F and G in the neighborhood of the neighboring block C which has been coded in spatial direct mode, and treats the forward motion vector MVFc and the backward motion vector MVBc indicated by the medians as motion vectors of the neighboring block C.

Also, the motion vector storage unit 706 stores motion vectors used for decoding a block which has been coded without using motion vectors of other blocks. To be more specific, in the situation as shown in FIG. 12, the motion vector storage unit 706 stores the motion vectors of the three blocks E, F and G in the neighborhood of the neighboring block C which has been coded in spatial direct mode. Therefore, when decoding the motion vector of the current block A, the motion vector decoding unit 711 calculates the motion vectors MVFc and MVBc for the neighboring block from the motion vectors of the above three blocks E, F and G stored in the motion vector storage unit 706. Note that the motion vector storage unit 706 may store in advance motion vectors obtained by calculating medians for decoding a block which has been coded using motion vectors of other blocks. In this case, in the situation as shown in FIG. 12, the motion vector storage unit 706 stores the motion vectors MVFc and MVBc in advance. Therefore, when decoding the motion vectors of the current block A, the motion vector decoding unit 711 does not need to calculate the motion vectors of the neighboring block C which has been coded in spatial direct mode, but can use the motion vectors MVFc and MVBc stored in the motion vector storage unit 706 directly as motion vectors of the neighboring block C.

Here, when motion vectors of a current block to be decoded are decoded, if previously decoded neighboring block of the current block has been processed in intra picture coding, not in inter picture coding as mentioned above, the moving picture decoding apparatus 700 performs exceptional processing.

For example, when one of three neighboring blocks has been intra picture coded, the motion vector decoding unit 711 of the moving picture decoding apparatus 700 performs processing considering the motion vectors of the neighboring block to be 0. When two neighboring blocks have been intra picture coded, the motion vector decoding unit 711 uses the motion vectors of the remaining one neighboring block as predictive values of the motion vectors of the current block. Further, when all the three neighboring blocks have been intra picture coded, the motion vector decoding unit 711 decodes the motion vectors of the current block considering predictive values thereof to be 0.

On the other hand, the coded prediction error data for the current macroblock in the picture B11 has been decoded in the prediction error decoding unit 702 and generated as a prediction error image, and the switches 709 and 710 are connected to the addition unit 708. Therefore, the motion compensation image generated based on the motion vector decoded by the motion vector decoding unit 711 is added to the prediction error image and outputted to the frame memory 707.

Decoding processing of the remaining macroblocks in the picture B11 is performed in the same manner. After the processing is completed for all the macroblocks in the picture B11, the decoding processing of the picture B12 follows.

As described above, according to the motion vector decoding method of the present invention, a predictive value is derived from motion vectors of previously decoded neighboring blocks, and a motion vector of each current block is decoded using the predictive value and the difference. If any of the neighboring blocks has been coded using motion vectors of other blocks, for example, in skip mode or direct mode, a predictive value is derived using, as a motion vector of the neighboring block, a motion vector calculated from the motion vectors of the other blocks for decoding that neighboring block.

Accordingly, motion vectors which have been coded in the manner as shown in the first embodiment can be decoded properly.

Note that, in the present embodiment, a case has been explained where a median calculated from motion vectors of previously decoded three neighboring blocks is used as a predictive value for decoding a motion vector, but any other number of neighboring blocks than three may be applied, and the predictive value may be determined by any other method. For example, a motion vector of an immediately left block may be used as a predictive value, or an average, instead of a median, may be used.

Figure 1:
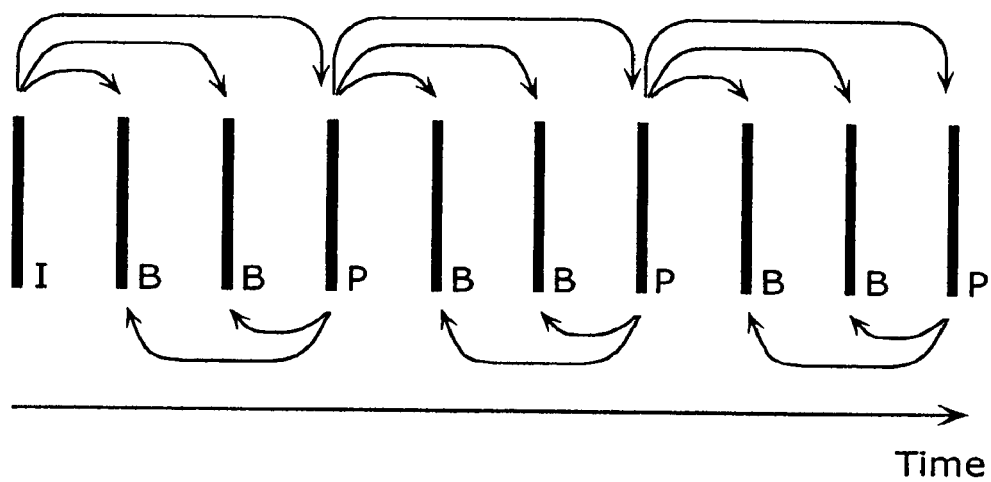
FIG. 1 is a diagram showing a predictive relation between pictures in a moving picture coding method.
Figure 2:
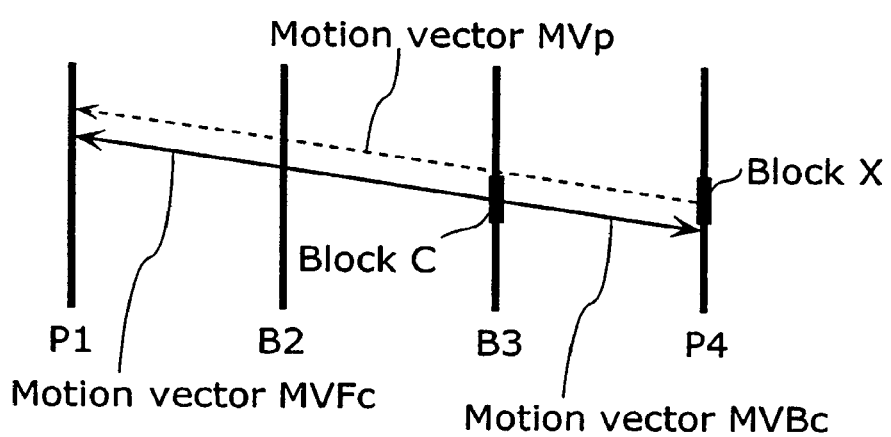
FIG. 2 is an illustration for explaining the inter picture prediction method in direct mode.
Figure 3A:
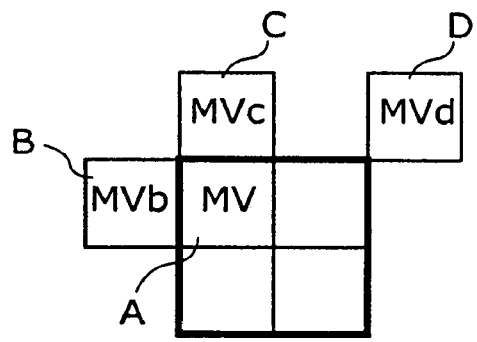
FIGS. 3A-3D are illustrations for explaining a method for coding a motion vector of a current block in MPEG-4.
Figure 3B:
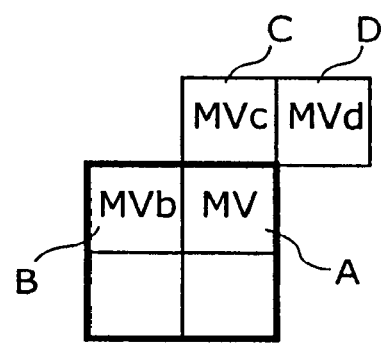
Figure 3C:
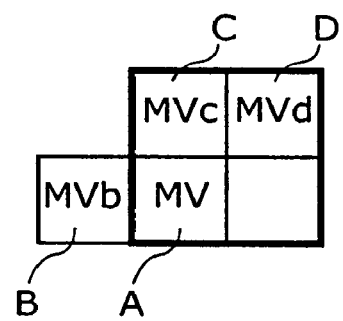
Figure 3D:
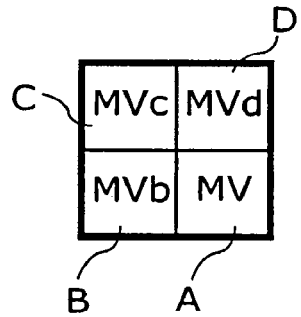
Figure 4:
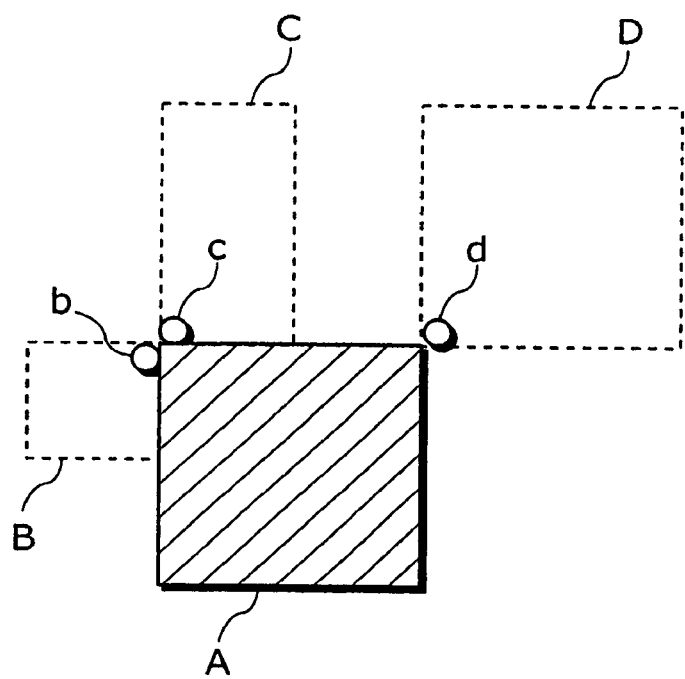
FIG. 4 is an illustration for explaining a method for coding a motion vector of a current block in H.26L.
Figure 5:
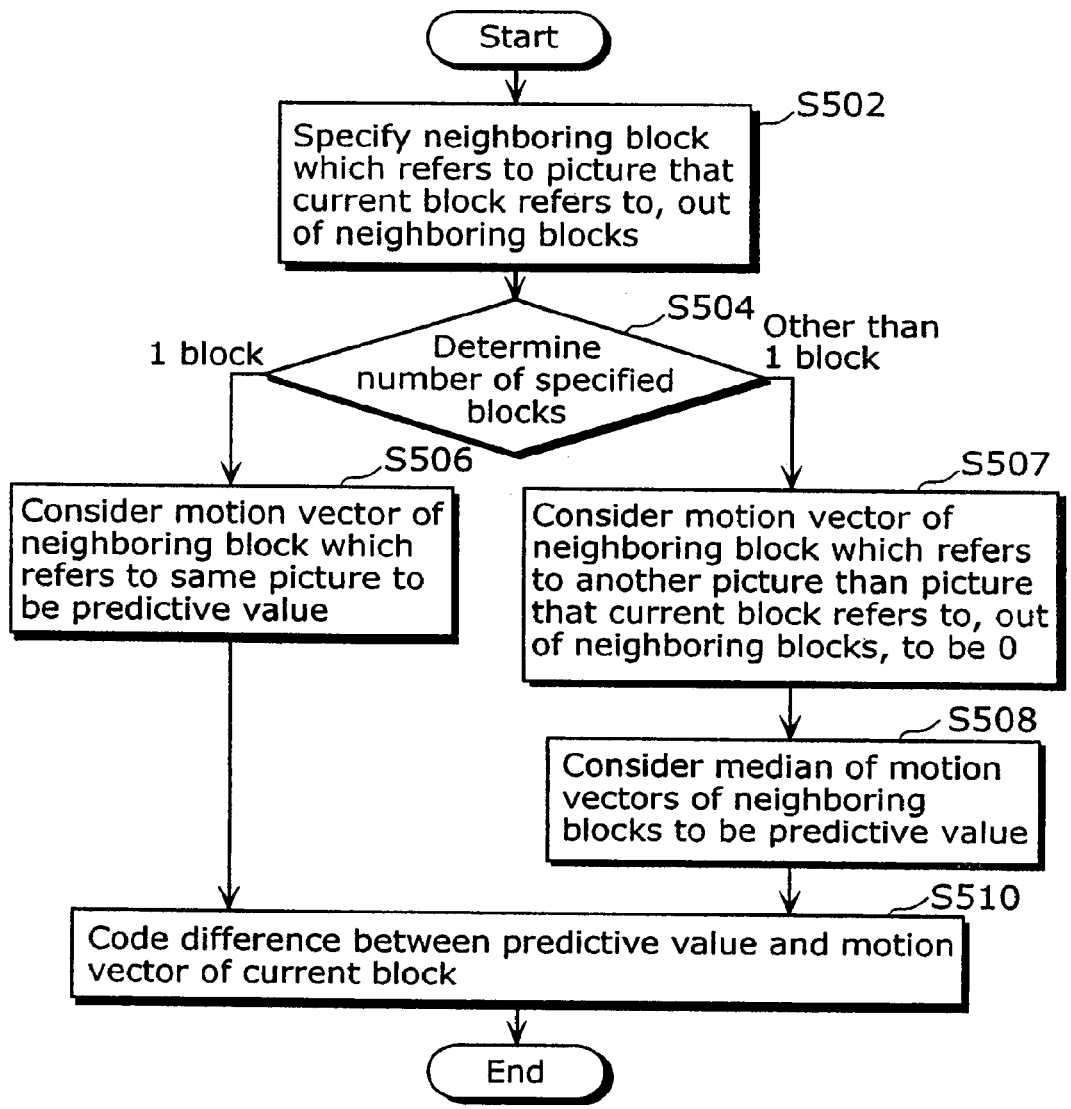
FIG. 5 is a flowchart showing the coding procedure in H26L.

Also, in the present embodiment, locations of neighboring blocks for decoding a motion vector has been explained using FIG. 3 and FIG. 4, but any other locations may be applied.

Also, in the present embodiment, a method for coding a current block using motion vectors of other blocks has been explained by taking skip mode and temporal and spatial direct modes as examples, but any other mode may be used.

Also, in the present embodiment, a case has been explained where a motion vector is decoded by adding a predictive value obtained from motion vectors of neighboring blocks and a difference as indicated in a bit stream, but any other method than addition may be used to decode the motion vector.

Also, in the present embodiment, a case has been explained where when a neighboring block has been coded in spatial direct mode, a median of motion vectors of previously coded three blocks in the neighborhood of the neighboring block is calculated and is treated as a motion vector of the neighboring block, but any other number of blocks than three may be used, and any other method may be used to determine the motion vector. For example, a motion vector of an immediately left block may be used as a motion vector of the neighboring block, or an average, instead of a median, may be used.

Also, in the present embodiment, when there exists a neighboring block which has been coded in spatial direct mode, two motion vectors of the block in the forward and backward directions are calculated, but two motion vectors in the forward direction only or two motion vectors in the backward direction only may be calculated. In this case, a current B-picture to be decoded refers to two pictures in the forward direction only or two pictures in the backward direction only.

Also, in the present embodiment, a case has been explained where one predetermined picture is referred to in decoding a P-picture (the picture P10 is referred to in decoding the picture P13, for example) and two predetermined pictures are referred to in decoding a B-picture (the pictures P10 and P13 are referred to in decoding the picture B11), but these P-picture and B-picture may be decoded by selecting reference pictures from among a plurality of pictures on every macroblock or block basis. In such a case, a predictive value of a motion vector can be generated in the manner as shown in FIG. 17.

FIG. 17 is a flowchart showing an operation of the motion vector decoding unit 711 for deriving a predictive value of a motion vector of a current block to be decoded and decoding the motion vector using the predictive value when a reference picture is selected on a block-by-block basis.

First, the motion vector decoding unit 711 specifies previously decoded three neighboring blocks of the current block (Step S400).

Then, the motion vector decoding unit 711 judges whether each of the specified neighboring blocks is a neighboring block Ba which has been coded using motion vectors of other blocks, or a neighboring block Bb which has been coded without using motion vectors of other blocks (Step S402).

Here, as for the neighboring block Ba, the motion vector decoding unit 711 obtains information indicating a motion vector used for decoding the neighboring block Ba and which reference picture it refers to, and treats the motion vector used for the decoding as a motion vector of the neighboring block Ba. As for the neighboring block Bb, the motion vector decoding unit 711 obtains information indicating the motion vector of the neighboring block Bb and which reference picture it refers to (Step S404).

Next, the motion vector decoding unit 711 specifies the neighboring block which refers to the picture that the current block refers to, out of the three neighboring blocks, based on the information obtained in Step S404 (Step S406), and determines the number of the specified neighboring blocks (Step S408).

If the number of the neighboring blocks determined in Step S408 is 1, the motion vector decoding unit 711 considers the motion vector of that one neighboring block which refers to the same picture to be a predictive value of the motion vector of the current block (Step S410).

If the number of the neighboring blocks determined in Step S408 is another number than one, the motion vector decoding unit 711 considers the motion vector of the neighboring block, out of the three neighboring blocks, which refers to another picture other than the current block refers to be 0 (Step S412), and considers the median of the motion vectors of the three neighboring blocks as a predictive value of the motion vector of the current block (Step S414).

As described above, the coded motion vector of the current block is decoded by adding the difference to the predictive value derived in Step S410 or Step S414.

Also, when a motion vector is decoded using a motion vector of a spatially adjacent block as a predictive value, an amount of motion vectors of 1 macroblock line (a portion of 1 macroblock high and a screen wide) needs to be stored in the motion vector storage unit 706 for decoding the motion vector, if the motion vectors which have been actually used for motion compensation in skip mode or direct mode are stored in the motion vector storage unit 706. This applies to the case where the motion vectors which have been actually used for motion compensation in skip mode or direct mode are stored in the motion vector storage unit 706. That is why when the neighboring blocks explained in connection with FIGS. 3A-3D and FIG. 4 of the present embodiment are used, there are past 1 macroblock slice of blocks which are referred to as neighboring blocks for decoding the motion vector, with the current macroblock as a starting point.

Third Embodiment

In addition, if a program for realizing the motion vector coding method or the motion vector decoding method as shown in each of the above-mentioned embodiments is recorded on a storage medium such as a flexible disk, it becomes possible to perform the processing as shown in each of the above embodiments easily in an independent computer system.

Figure 18A:
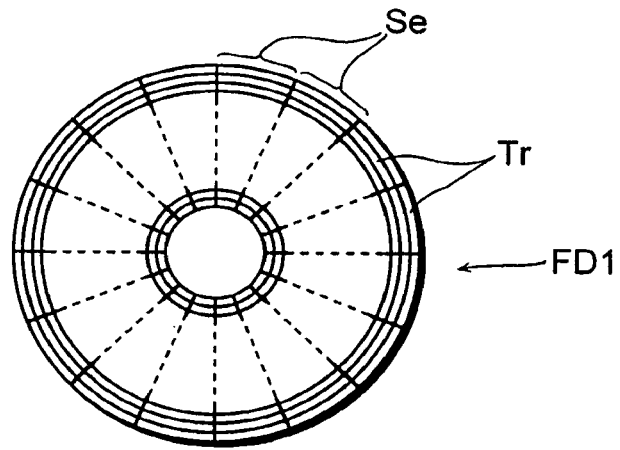
FIGS. 18A-18C are illustrations of a recording medium in a third embodiment of the present invention.
Figure 18B:
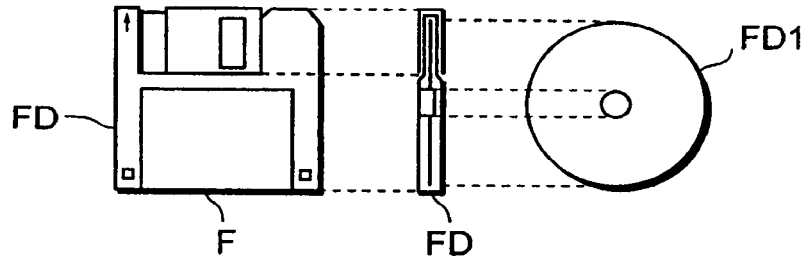
Figure 18C:
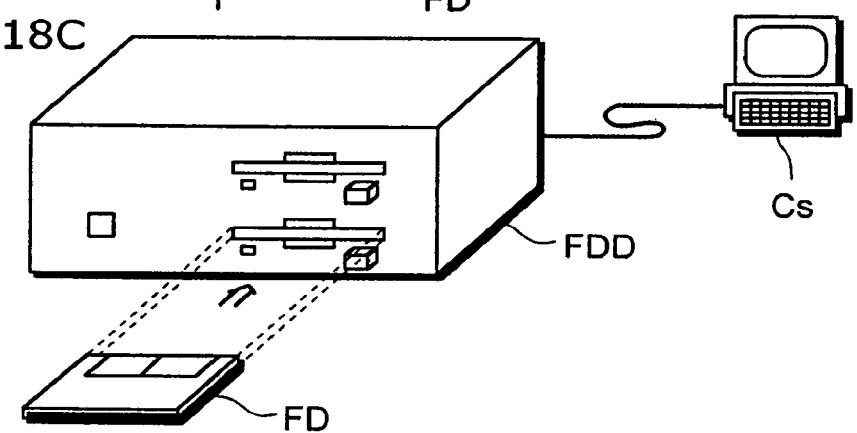

FIGS. 18A-18C are illustrations of a storage medium that stores a program for realizing the motion vector coding method and the motion vector decoding method executed by the moving picture coding apparatus 100 in the first embodiment and the moving picture decoding apparatus 200 in the second embodiment by a computer system.

FIG. 18B shows the front view and the cross-sectional view of the appearance of a flexible disk FD, and a disk FD1, and FIG. 18A shows an example of a physical format of the disk FD1 as a recording medium itself.

The disk FD1 is contained in a case F, a plurality of tracks Tr are formed concentrically on the surface of the disk FD1 in the radius direction from the periphery, and each track is divided into 16 sectors Se in the angular direction. Therefore, in the flexible disk storing the above-mentioned program, the motion vector coding method and the motion vector decoding method as the above program are recorded in an area allocated for it on the disk FD1.

FIG. 18C shows the structure for recording and reproducing the program on and from the flexible disk FD.

For recording the program on the flexible disk FD, the computer system Cs writes the motion vector coding method or the motion vector decoding method as the program on the flexible disk FD via a flexible disk drive FDD. For constructing the above motion vector coding method and the motion vector decoding method in the computer system Cs by the program recorded on the flexible disk FD, the program is read out from the flexible disk FD via the flexible disk drive FDD and transferred to the computer system Cs.

Note that the above explanation is made on the assumption that a recording medium is a flexible disk FD, but the same processing can also be performed using an optical disk. In addition, the recording medium is not limited to these, but any other mediums such as an IC card and a ROM cassette can be used in the same manner if a program can be recorded on them.

Fourth Embodiment

Further, the applications of the motion vector coding method and the motion vector decoding method as shown in the above embodiments and a system using them will be explained here.

Figure 19:
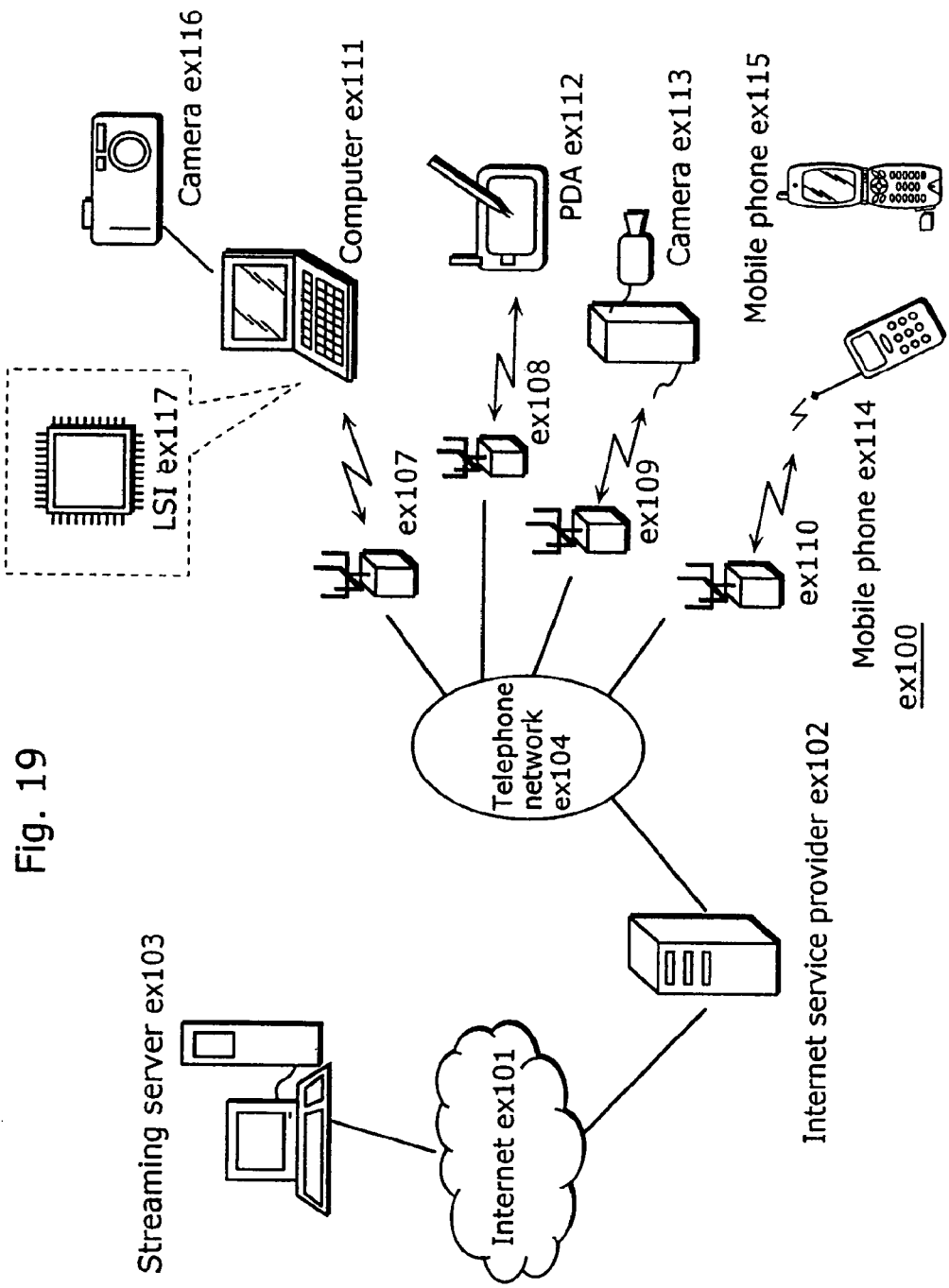
FIG. 19 is a block diagram showing an overall configuration of a content providing system in a fourth embodiment of the present invention.

FIG. 19 is a block diagram showing the overall configuration of a content providing system ex100 for realizing content distribution service. The area for providing communication service is divided into cells of desired size, and base stations ex107~ex110 which are fixed wireless stations are placed in respective cells In this content providing system ex100, various devices such as a computer ex111, a PDA (personal digital assistant) ex112, a camera ex113, a mobile phone ex114 and a camera-equipped mobile phone ex115 are connected to the Internet ex101, via an Internet service provider ex102, a telephone network ex104 and base stations ex107~ex110, for example.

However, the content providing system ex100 is not limited to the combination as shown in FIG. 19, and may be connected to a combination of any of them. Also, each device may be connected directly to the telephone network ex104, not through the base stations ex107~ex110 which are the fixed wireless stations.

The camera ex113 is a device such as a digital video camera capable of shooting moving pictures. The mobile phone may be any of a mobile phone of a PDC (Personal Digital Communications) system, a CDMA (Code Division Multiple Access) system, a W-CDMA (Wideband-Code Division Multiple Access) system or a GSM (Global System for Mobile Communications) system, a PHS (Personal Handyphone System) and the like.

Also, a streaming server ex103 is connected to the camera ex113 via the base station ex109 and the telephone network ex104, which enables live distribution or the like using the camera ex113 based on the coded data transmitted from the user. Either the camera ex113 or the server for transmitting the data may code the data shot by the camera. Also, the moving picture data shot by a camera ex116 may be transmitted to the streaming server ex103 via the computer ex111. The camera ex116 is a device such as a digital camera capable of shooting still and moving pictures. In this case, either the camera ex116 or the computer ex111 may code the moving picture data. An LSI ex117 included in the computer ex111 or the camera ex116 performs coding processing. Note that software for coding and decoding pictures may be integrated into any type of a storage medium (such as a CD-ROM, a flexible disk and a hard disk) that is a recording medium which can be read by the computer ex111 or the like. Furthermore, the camera-equipped mobile phone ex115 may transmit the moving picture data. This moving picture data is the data coded by the LSI included in the mobile phone ex115.

In this content providing system ex100, contents (such as a music live video) shot by users using the camera ex113, the camera ex116 or the like are coded in the same manner as the above embodiments and transmitted to the streaming server ex103, while the streaming server ex103 makes stream distribution of the above content data to the clients at their request. The clients include the computer ex111, the PDA ex112, the camera ex113, the mobile phone ex114 and so on capable of decoding the above-mentioned coded data. The content providing system ex100 is a system in which the clients can thus receive and reproduce the coded data, and further can receive, decode and reproduce the data in real time so as to realize personal broadcasting.

When each device in this system performs coding or decoding, the moving picture coding apparatus or the moving picture decoding apparatus as shown in each of the above-mentioned embodiments may be used.

A mobile phone will be explained as an example thereof.

Figure 20:
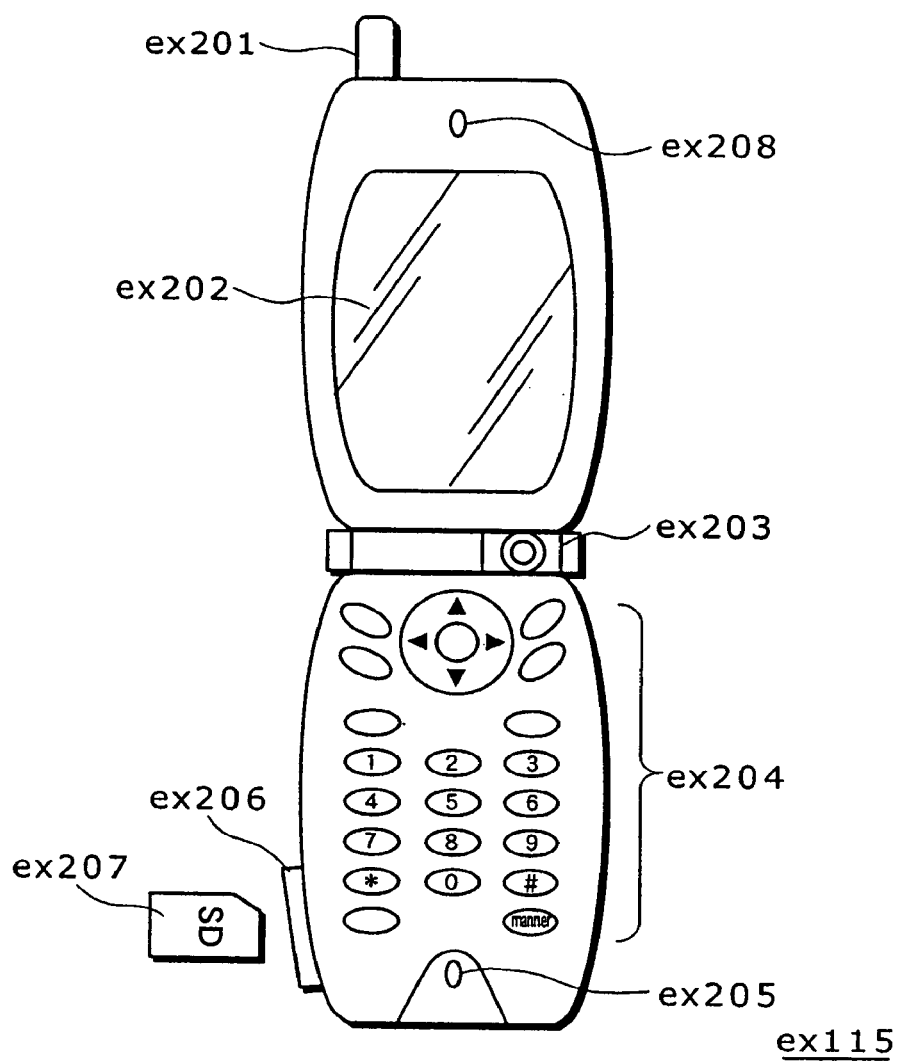
FIG. 20 is a front view of a mobile phone in the fourth embodiment.

FIG. 20 is a diagram showing a mobile phone ex115 which uses the motion vector coding method and the motion vector decoding method as explained in the above embodiments. The mobile phone ex115 has an antenna ex201 for sending and receiving radio waves between the base station ex110, a camera unit ex203 such as a CCD camera capable of shooting video and still pictures, a display unit ex202 such as a liquid crystal display for displaying the data obtained by decoding video shot by the camera unit ex203, video received by the antenna ex201, or the like, a main body including a set of operation keys ex204, a voice output unit ex208 such as a speaker for outputting voices, a voice input unit ex205 such as a microphone for inputting voices, a storage medium ex207 for storing coded or decoded data, such as data of moving or still pictures shot by the camera, and data of text, moving pictures or still pictures of received e-mails, and a slot unit ex206 for attaching the storage medium ex207 into the mobile phone ex115. The storage medium ex207 includes a flash memory element, a kind of EEPROM (Electrically Erasable and Programmable Read Only Memory) that is an electrically erasable and rewritable nonvolatile memory, in a plastic case such as an SD card.

Further, the mobile phone ex115 will be explained with reference to FIG. 21. In the mobile phone ex115, a main control unit ex311 for overall controlling each unit of the main body including the display unit ex202 and the operation keys ex204 is connected to a power supply circuit unit ex310, an operation input control unit ex304, a picture coding unit ex312, a camera interface unit ex303, an LCD (Liquid Crystal Display) control unit ex302, a picture decoding unit ex309, a multiplex/demultiplex unit ex308, a record/reproduce unit ex307, a modem circuit unit ex306 and a voice processing unit ex305 to each other via a synchronous bus ex313.

When a call-end key or a power key is turned ON by a user's operation, the power supply circuit unit ex310 supplies respective units with power from a battery pack so as to activate the camera-equipped digital mobile phone ex115 for a ready state.

In the mobile phone ex115, under the control of the main control unit ex311 including a CPU, ROM, RAM and the like, the voice processing unit ex305 converts the voice signals received by the voice input unit ex205 in conversation mode into digital voice data, the modem circuit unit ex306 performs spread spectrum processing of the digital voice data, and the send/receive circuit unit ex301 performs digital-to-analog conversion and frequency transformation of the data, so as to transmit the result via the antenna ex201. Also, in the mobile phone ex115, the data received by the antenna ex201 in conversation mode is amplified and performed of frequency transformation and analog-to-digital conversion, the modem circuit unit ex306 performs inverse spread spectrum processing of the data, and the voice processing unit ex305 converts it into analog voice data, so as to output the result via the voice output unit ex208.

Furthermore, when transmitting an e-mail in data communication mode, the text data of the e-mail inputted by operating the operation keys ex204 on the main body is sent out to the main control unit ex311 via the operation input control unit ex304. In the main control unit ex311, after the modem circuit unit ex306 performs spread spectrum processing of the text data and the send/receive circuit unit ex301 performs digital-to-analog conversion and frequency transformation of it, the result is transmitted to the base station ex110 via the antenna ex201.

When picture data is transmitted in data communication mode, the picture data shot by the camera unit ex203 is provided to the picture coding unit ex312 via the camera interface unit ex303. When the picture data is not transmitted, the picture data shot by the camera unit ex203 can also be displayed directly on the display unit 202 via the camera interface unit ex303 and the LCD control unit ex302.

The picture coding unit ex312, including the picture coding apparatus explained in the present invention, compress and codes the picture data provided from the camera unit ex203 by the coding method used for the picture coding apparatus as shown in the above-mentioned embodiments so as to transform it into coded picture data, and sends it out to the multiplex/demultiplex unit ex308. At this time, the mobile phone ex115 sends out the voices received by the voice input unit ex205 during picture pickup by the camera unit ex203 to the multiplex/demultiplex unit ex308 as digital voice data via the voice processing unit ex305.

The multiplex/demultiplex unit ex308 multiplexes the coded picture data provided from the picture coding unit ex312 and the voice data provided from the voice processing unit ex305 by a predetermined method, the modem circuit unit ex306 performs spread spectrum processing of the resulting multiplexed data, and the send/receive circuit unit ex301 performs digital-to-analog conversion and frequency transformation on the result for transmitting via the antenna ex201.

As for receiving data of a moving picture file which is linked to a Website or the like in data communication mode, the modem circuit unit ex306 performs inverse spread spectrum processing of the data received from the base station ex110 via the antenna ex201, and sends out the resulting multiplexed data to the multiplex/demultiplex unit ex308.

In order to decode the multiplexed data received via the antenna ex201, the multiplex/demultiplex unit ex308 demultiplexes the multiplexed data into a coded bit stream of picture data and a coded bit stream of voice data, and provides the coded picture data to the picture decoding unit ex309 and the voice data to the voice processing unit ex305 respectively via the synchronous bus ex313.

Next, the picture decoding unit ex309, including the picture decoding apparatus explained in the present invention, decodes the coded bit stream of the picture data by the decoding method paired with the coding method as shown in the above-mentioned embodiments, so as to generate reproduced moving picture data, and provides this data to the display unit ex202 via the LCD control unit ex302, and thus moving picture data included in a moving picture file linked to a Website, for instance, is displayed. At the same time, the voice processing unit ex305 converts the voice data into analog voice data, and provides this data to the voice output unit ex208, and thus voice data included in a moving picture file linked to a Website, for instance, is reproduced.

Figure 22:
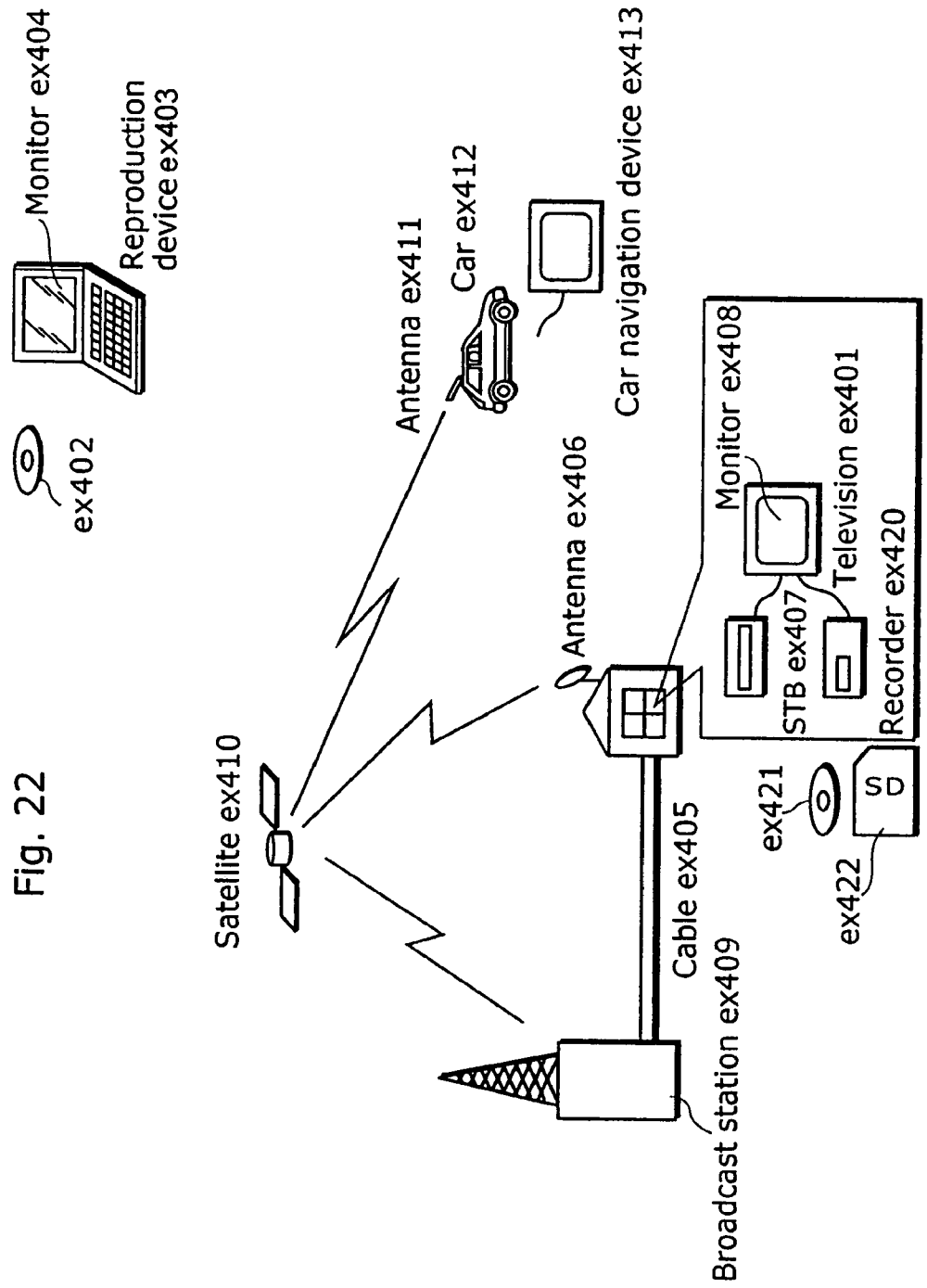
FIG. 22 is a block diagram showing an overall configuration of a digital broadcasting system in the fourth embodiment.

The present invention is not limited to the above-mentioned system. Ground-based or satellite digital broadcasting has been in the news lately, and at least either the picture coding apparatus or the picture decoding apparatus in the above-mentioned embodiments can be incorporated into such a digital broadcasting system as shown in FIG. 22. More specifically, a coded bit stream of video information is transmitted from a broadcast station ex409 to or communicated with a broadcast satellite ex410 via radio waves. Upon receipt of it, the broadcast satellite ex410 transmits radio waves for broadcasting, a home antenna ex406 with a satellite broadcast reception function receives the radio waves, and an apparatus such as a television (receiver) ex401 or a set top box (STB) ex407 decodes the coded bit stream for reproduction. The picture decoding apparatus as shown in the above-mentioned embodiments can be implemented in the reproduction device ex403 for reading a coded bit stream recorded on a storage medium ex402 such as a CD and DVD that is a recording medium and decoding it. In this case, the reproduced video signals are displayed on a monitor ex404. It is also conceived to implement the picture decoding apparatus in the set top box ex407 connected to a cable ex405 for a cable television or the antenna ex406 for satellite and/or ground-based broadcasting so as to reproduce them on a monitor ex408 of the television. The picture decoding apparatus may be incorporated into the television, not in the set top box. Or, a car ex412 having an antenna ex411 can receive signals from the satellite ex410, the base station ex107 or the like for reproducing moving pictures on a display apparatus such as a car navigation device ex413 or the like in the car ex412.

Furthermore, the picture coding apparatus as shown in the above-mentioned embodiments can code picture signals for recording them on a recording medium. As a concrete example, there is a recorder ex420 such as a DVD recorder for recording picture signals on a DVD disk ex421 and a disk recorder for recording them on a hard disk. They can also be recorded on an SD card ex422. If the recorder ex420 includes the picture decoding apparatus as shown in the above-mentioned embodiments, the picture signals recorded on the DVD disk ex421 or the SD card ex422 can be reproduced for display on the monitor ex408.

Figure 21:
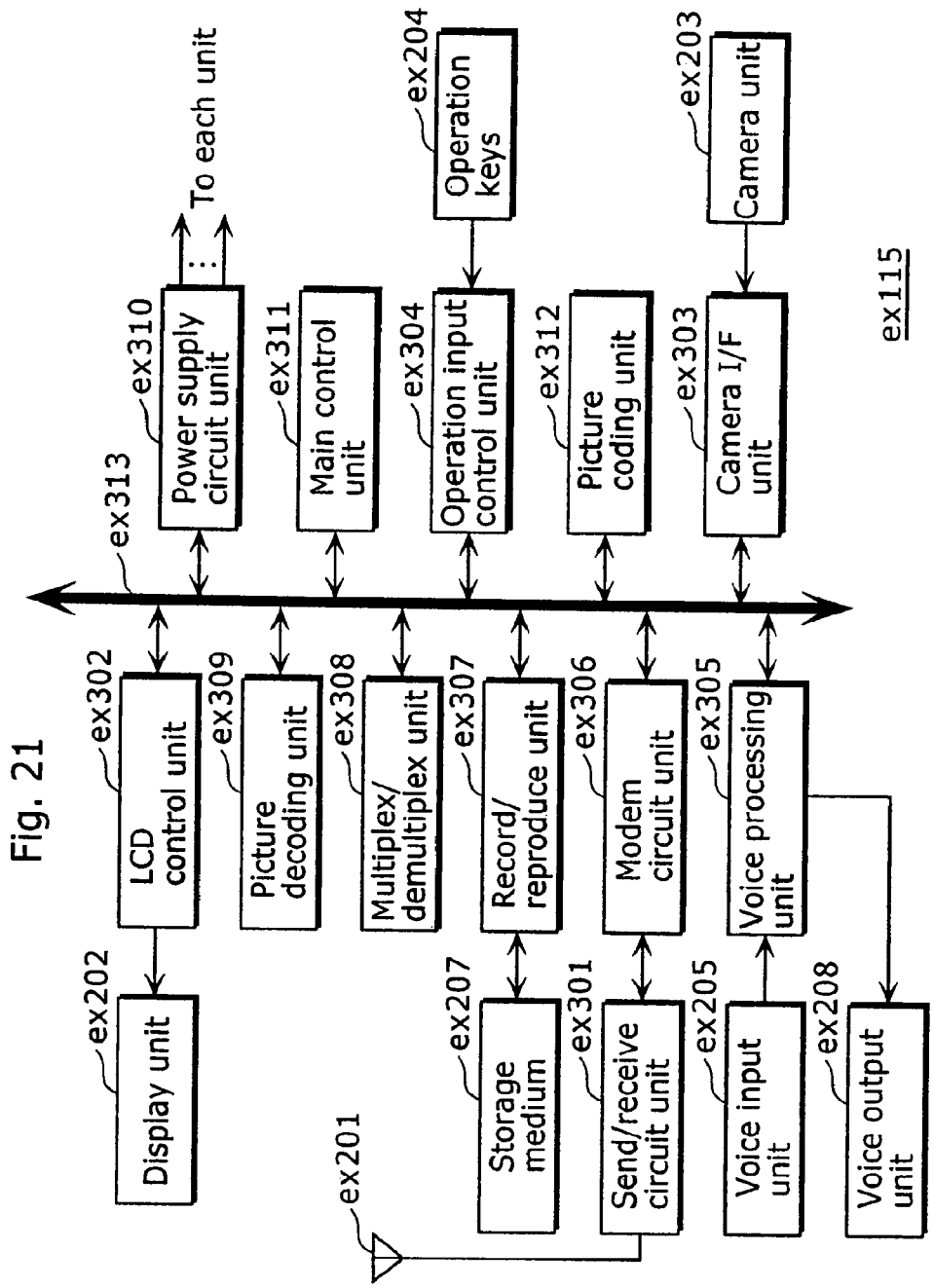
FIG. 21 is a block diagram of the mobile phone in the fourth embodiment.

Note that as the structure of the car navigation device ex413, the structure without the camera unit ex203, the camera interface unit ex303 and the picture coding unit ex312, out of the units as shown in FIG. 21, is conceivable. The same applies to the computer ex111, the television (receiver) ex401 and others.

In addition, three types of implementations can be conceived for a terminal such as the above-mentioned mobile phone ex114; a sending/receiving terminal equipped with both an encoder and a decoder, a sending terminal equipped with an encoder only, and a receiving terminal equipped with a decoder only.

As described above, it is possible to use the motion vector coding method or the motion vector decoding method as shown in the above embodiments in any of above-mentioned devices and systems, and thus the effects explained in the above embodiments can be obtained.

The motion vector coding method and the motion vector decoding method according to the present invention are suitable for use in a moving picture coding apparatus for coding moving pictures, a moving picture decoding apparatus for decoding coded moving pictures, and a system including these apparatuses, such as a content providing system for providing contents like digital works, for example, and a digital broadcasting system.

The invention claimed is:

1. A motion vector decoding method for decoding a motion vector of a current block in a moving picture, the method comprising:
   a neighboring block specification step of specifying three neighboring blocks, the three neighboring blocks being located in a neighborhood of the current block and having been already decoded;
   a first judgment step of judging whether or not each of the three neighboring blocks has been decoded using a motion vector of another block;
   a second judgment step of judging whether or not a reference picture referred to in the decoding of the current block is the same as each of a reference picture referred to in the decoding of the three neighboring blocks;
   a different motion vector determining step of determining a different motion vector of each of the three neighboring blocks based on a result of the first judgment step;
   a prediction step of deriving a predictive motion vector of the current block using different motion vectors of the three neighboring blocks based on a result of the second judgment step;
   a decoding step of decoding a coded motion vector to obtain a decoded difference motion vector of the current block; and a motion vector recovering step of recovering the motion vector of the current block by adding the decoded difference motion vector of the current block and the predictive motion vector, wherein, in the different motion vector determining step of determining a different motion vector of each of the three neighboring blocks, (1) a motion vector, which is calculated from the motion vector of the other block and which is used in performing a decoding process on a neighboring block of the three neighboring blocks, is determined as a different motion vector of the neighboring block when it is judged in the first judgment step that the neighboring block has been decoded using the motion vector of the other block, and (2) a motion vector, which is detected for the neighboring block and which is used in performing a decoding process on the neighboring block, is determined as a different motion vector of the neighboring block when it is judged in the first judgment step that the neighboring block has not been decoded using the motion vector of the other block,
   wherein, in the prediction step of deriving a predictive motion vector of the current block, (1) when it is judged in the second judgment step that three neighboring blocks refer to the same reference picture as the current block, the predictive motion vector of the current block is set to a median of three motion vectors of the three neighboring blocks, and (2) when it is judged in the second judging step that only one of the three neighboring blocks refer to the same reference picture as the current block, the predictive motion vector of the current block is set to be a motion vector of the only one neighboring block having the same reference picture as the current block.

2. A motion vector decoding apparatus for decoding a motion vector of a current block in a moving picture, the apparatus comprising:

a non-transitory memory storing a program; and
a hardware processor that executes the program and causes the motion vector decoding apparatus to operate as:
a neighboring block specification unit operable to specify three neighboring blocks, the three neighboring blocks being located in a neighborhood of the current block and have been already decoded;
a first judgment unit operable to judge whether or not each of the three neighboring blocks has been decoded using a motion vector of another block; a second judgment unit operable to judge whether or not a reference picture referred to in the decoding of the current block is the same as a reference picture referred to in the decoding of each of the three neighboring blocks;
a different motion vector determining unit operable to determine a different motion vector of each of the three neighboring blocks based on a result of the first judgment unit;
a prediction unit operable to derive a predictive motion vector of the current block using different motion vectors of the three neighboring blocks based on a result of the second judgment unit;
a decoding unit operable to decode a coded motion vector to obtain a decoded difference motion vector of the current block; and a motion vector recovering unit operable to recover the motion vector of the current block by adding the decoded difference motion vector and the predictive motion vector, wherein, the different motion vector determining unit is further operable to: (1) determine a motion vector, which is calculated from the motion vector of the other block and which is used in performing a decoding process on a neighboring block of the three neighboring blocks, as a different motion vector of the neighboring block when it is judged by the first judgment unit that the neighboring block has been decoded using the motion vector of the other block, and (2) determine a motion vector, which is detected for the neighboring block and which is used in performing a decoding process on the neighboring block, as a different motion vector of the neighboring block when it is judged by the first judgment unit that the neighboring block has not been decoded using the motion vector of the other block, wherein, the prediction unit is further operable to: (1) set the predictive motion vector of the current block to a median of three motion vectors of the three neighboring blocks when it is judged by the second judgment unit that the three neighboring blocks refer to the same reference picture as the current block, and (2) set the predictive motion vector of the current block to a motion vector of one neighboring block having the same reference picture as the current block when it is judged by the second judging unit that only one of the three neighboring blocks refer to the same reference picture as the current block.

* * * * *